US009670301B2

(12) United States Patent
Furukawa et al.

(10) Patent No.: US 9,670,301 B2
(45) Date of Patent: Jun. 6, 2017

(54) COPOLYMER HAVING CARBOSILOXANE DENDRIMER STRUCTURE AND HYDROPHILIC GROUP

(71) Applicant: DOW CORNING TORAY CO., LTD., Tokyo (JP)

(72) Inventors: Haruhiko Furukawa, Chiba (JP); Akito Hayashi, Chiba (JP); Tomohiro Iimura, Chiba (JP)

(73) Assignee: Dow Corning Toray Co., Ltd., Tokyo (JP)

( * ) Notice: Subject to any disclaimer, the term of this patent is extended or adjusted under 35 U.S.C. 154(b) by 0 days.

(21) Appl. No.: 14/422,773

(22) PCT Filed: Aug. 22, 2013

(86) PCT No.: PCT/JP2013/073069
§ 371 (c)(1),
(2) Date: Feb. 20, 2015

(87) PCT Pub. No.: WO2014/030770
PCT Pub. Date: Feb. 27, 2014

(65) Prior Publication Data
US 2015/0232601 A1    Aug. 20, 2015

(30) Foreign Application Priority Data
Aug. 22, 2012   (JP) ................. 2012-182828

(51) Int. Cl.
| C08F 230/08 | (2006.01) |
| A61K 8/895 | (2006.01) |
| C08F 214/18 | (2006.01) |
| C08L 91/00 | (2006.01) |
| C08L 43/04 | (2006.01) |
| A61Q 19/10 | (2006.01) |
| A61Q 1/14 | (2006.01) |
| A61Q 19/00 | (2006.01) |
| A61Q 1/02 | (2006.01) |
| A61Q 1/12 | (2006.01) |
| A61Q 1/08 | (2006.01) |
| A61Q 1/04 | (2006.01) |
| A61Q 1/06 | (2006.01) |
| A61Q 1/10 | (2006.01) |
| A61Q 15/00 | (2006.01) |
| A61Q 17/04 | (2006.01) |
| A61Q 5/00 | (2006.01) |
| A61Q 5/02 | (2006.01) |
| A61Q 5/06 | (2006.01) |

(52) U.S. Cl.
CPC .......... *C08F 230/08* (2013.01); *A61K 8/895* (2013.01); *A61Q 1/02* (2013.01); *A61Q 1/04* (2013.01); *A61Q 1/06* (2013.01); *A61Q 1/08* (2013.01); *A61Q 1/10* (2013.01); *A61Q 1/12* (2013.01); *A61Q 1/14* (2013.01); *A61Q 5/00* (2013.01); *A61Q 5/02* (2013.01); *A61Q 5/06* (2013.01); *A61Q 5/065* (2013.01); *A61Q 15/00* (2013.01); *A61Q 17/04* (2013.01); *A61Q 19/00* (2013.01); *A61Q 19/10* (2013.01); *C08F 214/182* (2013.01); *C08L 43/04* (2013.01); *C08L 91/00* (2013.01)

(58) Field of Classification Search
CPC ......... A61K 8/891; A61K 8/895; C08L 83/06; C08L 83/12; C08G 77/442
USPC ......... 514/772; 524/268, 544, 547; 526/245, 526/246, 279
See application file for complete search history.

(56) References Cited

U.S. PATENT DOCUMENTS

| 4,980,167 A | 12/1990 | Harashima et al. |
| 5,628,989 A | 5/1997 | Harashima et al. |
| 5,939,478 A | 8/1999 | Beck et al. |

(Continued)

FOREIGN PATENT DOCUMENTS

| CN | 101084863 A | 12/2007 |
| CN | 101472979 A | 7/2009 |

(Continued)

OTHER PUBLICATIONS

PCT/JP2013/073069 International Search Report dated Mar. 5, 2014, 3 pages.

(Continued)

*Primary Examiner* — Porfirio Nazario Gonzalez
(74) *Attorney, Agent, or Firm* — Warner Norcross & Judd LLP

(57) ABSTRACT

Problem: To provide a novel copolymer capable of use as a surface treatment agent which is safe and does not generate hydrogen, which has good compatibility with other cosmetic raw materials so as to be able to improve compounding stability of a cosmetic, which contributes to good water resistance, sebum resistance, gloss, feel, hair attachment ability, skin attachment ability and the like of a cosmetic, which further may be used for treatment of powders of a wide range of cosmetics, and which nearly entirely suppresses the occurrence of dispersion failure on the skin.

Resolution Means: A copolymer comprising: (A) an unsaturated monomer having a carbosiloxane dendrimer structure; and (B) an unsaturated monomer having at least one hydrophilic group in the molecule.

A content of the unsaturated monomer having the carbosiloxane dendrimer structure is in the range of 35 to 50% by mass of the total monomer units of the copolymer. The present invention is also a liquid composition, surface treatment agent, and powder composition including such a copolymer, as well as a cosmetic raw material containing such components.

16 Claims, No Drawings

(56) References Cited

U.S. PATENT DOCUMENTS

| | | |
|---|---|---|
| 6,238,656 B1 | 5/2001 | Morita et al. |
| 6,280,748 B1 | 8/2001 | Morita et al. |
| 7,488,492 B2 | 2/2009 | Furukawa et al. |
| 7,722,899 B2 | 5/2010 | Ono et al. |
| 2012/0251605 A1 | 10/2012 | Iimura et al. |
| 2012/0263662 A1 | 10/2012 | Iimura et al. |

FOREIGN PATENT DOCUMENTS

| | | |
|---|---|---|
| JO | H05237360 A | 9/1993 |
| JP | H0225411 A | 1/1990 |
| JP | 2243612 A | 9/1990 |
| JP | H02-243612 A | 9/1990 |
| JP | H07-196946 A | 8/1995 |
| JP | H08-12524 A | 1/1996 |
| JP | H08-12545 A | 1/1996 |
| JP | H08-12546 A | 1/1996 |
| JP | H09-136812 A | 5/1997 |
| JP | H09171154 A | 6/1997 |
| JP | H09-241511 A | 9/1997 |
| JP | H10-36219 A | 2/1998 |
| JP | H11-001530 A | 1/1999 |
| JP | H11-193331 A | 7/1999 |
| JP | 2000-063225 A | 2/2000 |
| JP | 2000119139 A | 4/2000 |
| JP | 2000226551 A | 8/2000 |
| JP | 2000-281523 A | 10/2000 |
| JP | 2003-226611 A | 8/2003 |
| JP | 4009382 B2 | 9/2007 |
| JP | 2007532754 | 11/2007 |
| JP | 201018612 A | 1/2010 |
| JP | 2010143833 A | 7/2010 |
| JP | 2011016733 A | 1/2011 |
| JP | 2011-148784 A | 8/2011 |
| JP | 2011-149017 A | 8/2011 |
| JP | 2011246704 A | 12/2011 |
| JP | 2011246705 A | 12/2011 |
| JP | 2011246706 A | 12/2011 |
| JP | 2012118510 A | 6/2012 |
| JP | 2012136677 A | 7/2012 |
| WO | WO02100356 A1 | 12/2002 |
| WO | WO02100356 A1 | 12/2002 |
| WO | WO2006106728 A | 10/2006 |
| WO | WO2009022621 A1 | 2/2009 |
| WO | WO2009142047 A1 | 11/2009 |
| WO | WO2011049246 A1 | 4/2011 |
| WO | WO2011049248 A1 | 4/2011 |
| WO | WO2011078407 A1 | 6/2011 |
| WO | WO2012091161 A2 | 7/2012 |

OTHER PUBLICATIONS

English language abstract and machine assisted English translation for JPH07-196946 extracted from http://www4.ipdl.inpit.go.jp/ database on Feb. 12, 2015, 10 pages.

English language abstract and machine assisted English translation for JPH08-12524 extracted from http://www4.ipdl.inpit.go.jp/ database on Feb. 17, 2015, 9 pages.

English language abstract and machine assisted English translation for JPH08-12546 extracted from http://www4.ipdl.inpit.go.jp/ database on Feb. 17, 2015, 9 pages.

English language abstract and machine assisted English translation for JPH09-136812 extracted from http://www4.ipdl.inpit.go.jp/ database on Feb. 17, 2015, 12 pages.

English language abstract and machine assisted English translation for JPH11-001530 extracted from http://www4.ipdl.inpit.go.jp/ database on Feb. 20, 2015, 15 pages.

English language abstract and machine assisted English translation for JPH09-241511 extracted from http://www4.ipdl.inpit.go.jp/ database on Feb. 17, 2015, 8 pages.

English language abstract and machine assisted English translation for JPH10-36219 extracted from http://www4.ipdl.inpit.go.jp/ database on Feb. 17, 2015, 13 pages.

COPOLYMER HAVING CARBOSILOXANE DENDRIMER STRUCTURE AND HYDROPHILIC GROUP

TECHNICAL FIELD

The present invention relates to a novel copolymer that has a carbosiloxane dendrimer structure and hydrophilic group in the molecule, and the present invention preferably relates to a copolymer that further has a fluorine-containing organic group in the molecule. Moreover, the present invention also relates to a liquid composition, surface treatment agent, and powder composition that include this copolymer. The present invention also relates to a cosmetic raw material that includes this liquid composition, surface treatment agent, or powder composition.

BACKGROUND ART

Methylhydrogenpolysiloxanes are widely used as various types of surface treatment agents used for cosmetics. A powder that has been treated using methylhydrogenpolysiloxane is highly water repellant and thus is characterized as improving the ability to prevent the smearing of makeup. However, in addition to reacting with the particle surface at the time of surface treatment, methylhydrogenpolysiloxane also triggers crosslinking reactions between molecules. Thus the percentage of reaction with the surface is low, and this results in remnant unreacted Si—H bonds in the surface-treated powder. Thus, depending on conditions, there is the possibility of generating hydrogen gas, and such hydrogen gas is dangerous in the presence of fire or the like. Further, various types of problems have occurred due to use of methylhydrogenpolysiloxane, such as expansion of cosmetic containers, clouding of compact mirrors, and the like. Various methods have been proposed so that remnant Si—H bonds are not generated. Such methods include a method of surface treatment using a single end alkoxy-modified silicone as described in Japanese Unexamined Patent Application Publication No. H07-196946, and a method of surface treatment using an acrylic-modified silicone having an alkoxysilyl group as described in WO 2002/100356. However, the alkoxy group content is low when the single end alkoxy-modified silicone is used, and thus the method using the single end alkoxy-modified silicone has had a problem of low reactivity with the powder. On the other hand, the method of surface treatment using the acrylic-modified silicone having an alkoxysilyl group uses an acrylic-modified silicone produced by grafting a linear silicone to an acrylic main chain, and thus there has been a problem of insufficient sebum resistance and the like. Moreover, the powder that has been surface-treated using the acrylic-modified silicone having an alkoxysilyl group has had problems in that compatibility with other cosmetic raw materials is low, and compounding stability of the cosmetic has been poor.

Cosmetic raw materials have been proposed that have, as a main agent, a vinyl-based polymer that has a carbosiloxane dendrimer structure, or a vinyl-based polymer that has both a carbosiloxane dendrimer structure and a fluorine-containing organic group (see Japanese Unexamined Patent Application Publication No. 2000-063225 and Japanese Unexamined Patent Application Publication No. 2003-226611). However, in Japanese Unexamined Patent Application Publication No. 2000-063225 and Japanese Unexamined Patent Application Publication No. 2003-226611, there is no mention of use in surface treatment of various types of powders.

Moreover, Japanese Unexamined Patent Application Publication No. H09-136812 proposes a copolymer that is obtained by copolymerization of a radical-polymerizable monomer, an organopolysiloxane compound that has a radial-polymerizable group at one molecular chain terminal, and N-vinylpyrrolidone. However, this copolymer has no hydrophilic group, the copolymer particularly does not have an alcoholic hydroxyl group, and there is no description of use in the surface treatment of various types of powders.

Further, although the blending of the copolymer in a cosmetic as a film-forming agent is disclosed, the copolymer has had a problem in that dispersibility and compounding stability are insufficient particularly when the copolymer is used with a powder used in cosmetics. In order to solve such problems, the authors of the present application propose a cosmetic raw material and powder treatment using a specific polymer having a carbosiloxane dendrimer structure in Japanese Unexamined Patent Application Publication No. 2011-149017 and Japanese Unexamined Patent Application Publication No. 2011-148784. In comparison to previously existing powder treatment agents, these polymers have greatly superior dispersibility, compounding stability in the cosmetic, or the like. However, these polymers still have margin for improvement in dispersion performance particularly when a fluorine-treated powder or the like is blended in the cosmetic. Also after the cosmetic containing the powder has been coated onto the skin, sometimes dispersion failure occurs on the skin, i.e. agglomeration of the powder due to volatilization of a liquid oil agent or the like. Further, there has been neither mention nor suggestion concerning the relative proportion of the specified carbosiloxane dendrimer structure composing the copolymer. Also there has been neither mention nor suggestion concerning combined use with a monomer that has a hydrophilic functional group.

PRIOR ART DOCUMENTS

Patent Documents

Patent Document 1: Japanese Unexamined Patent Application Publication No. H07-196946 A
Patent Document 2: WO2002/100356
Patent Document 3: Japanese Unexamined Patent Application Publication No. 2000-063225A
Patent Document 4: Japanese Unexamined Patent Application Publication No. 2003-226611 A
Patent Document 5: Japanese Unexamined Patent Application Publication No. H09-136812A
Patent Document 6: Japanese Unexamined Patent Application Publication No. 2011-148784A
Patent Document 7: Japanese Unexamined Patent Application Publication No. 2011-149017A

SUMMARY OF INVENTION

Technical Problem

In consideration of the aforementioned circumstances of the conventional technology, an object of the present invention is to provide a novel copolymer that is safe and does not generate hydrogen, that has good compatibility with other cosmetic raw materials, so that it is possible to improve compounding stability in a cosmetic, and so that it is possible to impart to the cosmetic good water resistance, sebum resistance, gloss, feel, attachment to hair and skin, or the like, as well as to be able to use the copolymer in the treatment of a wide range of powders used for cosmetics, and to use the copolymer as a surface treatment agent that is capable of nearly entirely suppressing failure of dispersion when applied on the skin. Another object of the present invention is to provide a surface treatment agent that includes the copolymer and a powder composition that has undergone surface treatment using the copolymer or the like. Yet another object of the present invention is to provide a cosmetic raw material by blending such copolymers or the like.

Solution to Problem

The object of the present invention is achieved by a copolymer comprising: (A) an unsaturated monomer having a carbosiloxane dendrimer structure represented by the following formula (1):

[Formula 3]

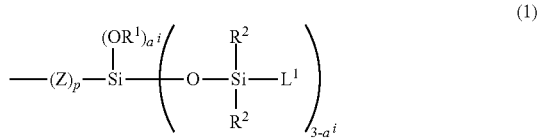

in the formula,
Z is a divalent organic group;
p is 0 or 1;
$R^1$ and $R^2$ each independently represent a group selected from the group consisting of alkyl groups, aryl groups, and aralkyl groups, having 1 to 10 carbon atoms; and
$L^1$ is a silylalkyl group, in the case of i=1, represented by the following formula (2):

[Formula 4]

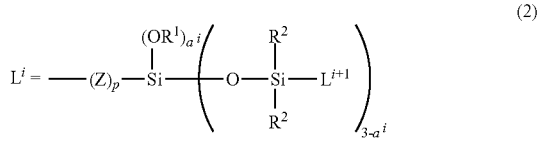

in the formula,
Z and p are the same as defined above;
$R^1$ and $R^2$ are the same as defined above;
i is an integer ranging from 1 to 10 indicating a total number of generations of the silylalkyl group;
$L^{i+1}$ is a group selected from the group consisting of a hydrogen atom, alkyl groups, aryl groups, and aralkyl groups, having 1 to 10 carbon atoms, and the silylalkyl groups; however, in the case of i=c (c is an integer ranging from 1 to 10 indicating the number of generations of the silylalkyl group),
$L^{i+1}$ is a group selected from the group consisting of a hydrogen atom, alkyl groups, aryl groups, and aralkyl groups, having 1 to 10 carbon atoms; and in the case of i<c, $L^{i+1}$ is the silylalkyl group; and
$a^i$ is an integer ranging from 0 to 3; and
(B) an unsaturated monomer having at least one hydrophilic group in the molecule;
the content of the unsaturated monomer having the carbosiloxane dendrimer structure being 35 to 50% by mass of the total monomer.

Moreover, the inventors attained the present invention by discovery of the ability to better solve the aforementioned problems by a copolymer that is obtained by copolymerizing the (A) unsaturated monomer having the carbosiloxane dendrimer structure,
the (B) unsaturated monomer having at least one hydrophilic group in the molecule, and
the (C) unsaturated monomer having at least one fluorine-containing organic group in the molecule, at mass ratio ranges such that {component (A) mass content/total monomer mass content}:{component (B) mass content/total monomer mass content}:{component (C) mass content/total monomer mass content} are in the ranges of [0.35 to 0.50:0.01 to 0.40:0.00 to 0.60], respectively;
and the following condition is fulfilled: {component (A) mass content/total monomer mass content}≥{component (B) mass content/total monomer mass content}.

In particular, the inventors of the present invention attained the present invention by the discovery of the ability to solve the aforementioned problems particularly well by a copolymer obtained by copolymerizing the (A) unsaturated monomer having the carbosiloxane dendrimer structure,
the (B1) unsaturated monomer having at least one monohydric or polyhydric alcoholic hydroxyl group in the molecule, and
(C1) an unsaturated monomer represented by the general formula:

wherein, $R^{15}$ is a hydrogen atom or methyl group; $R^f$ is a fluoroalkyl group or fluoroalkyloxyfluoroalkylene group,
at mass ratio ranges such that {component (A) mass content/total monomer mass content}:{component (B) mass content/total monomer mass content}:{component (C1) mass content/total monomer mass content} are in the ranges of [0.35 to 0.50:0.10 to 0.40:0.10 to 0.50], respectively;
and the following condition is fulfilled: {component (A) mass content/total monomer mass content}≥{component (B) mass content/total monomer mass content}.

The object of the present invention is finally obtained by use of a surface treatment agent that includes the aforementioned novel copolymer, by use of a powder that has undergone surface treatment by the aforementioned novel copolymer, and by use of such components as cosmetic raw materials.

The novel copolymer further preferably is used in the form of a liquid composition that includes (D) at least one type of oil agent. This oil agent is further preferably a hydrophobic silicone oil that has a viscosity of 0.65 to 100,000 mm²/s at 25° C. The novel copolymer is particularly preferably used in the form of a liquid composition that includes a volatile silicone oil (e.g. decamethyl cyclopentasiloxane or the like) or a hydrocarbon oil, such as isododecane and the like.

The novel copolymer or the liquid composition may be used as a surface treatment agent for a powder or the like. In particular, a powder composition form is preferably used that includes the novel copolymer and (E) at least one type of powder or coloring agent. The powder or the like may be at least one type selected from the group of inorganic pigment powders, organic pigment powders, and resin powders having an average particle diameter in the range of 1 nm to 20 μm. At least part of the powder and/or the coloring agent may have been subjected to water-proofing treatment by a surface treatment agent other than the copolymer of the present invention. The aforementioned powder or coloring agent is preferably (E1) a water-repellency treated powder or coloring agent.

Advantageous Effects of Invention

When the novel polymer of the present invention is used as a surface treatment agent or cosmetic raw material, the novel polymer of the present invention may be used with advantage for imparting water repellency to the surface of a powder or the like, and safety is excellent due to the lack of generation of hydrogen. Further, the novel copolymer of the present invention is used as a copolymer that has a hydrophilic group and that has non-linear (i.e. highly branched) dendrimer-like silicone multi-grafted to the main chain. Therefore compatibility with various types of other cosmetic raw materials is good, and thus compounding stability of the cosmetic or the like is excellent. Further, the novel copolymer of the present invention is able to be used for the treatment of a wide range of powders or the like used in cosmetics. Further, when applied to the skin, the novel copolymer of the present invention is capable of nearly completely suppressing dispersion failure of the powder or the like after volatilization of an oil agent. It is thus possible to provide a surface treatment agent that includes this copolymer and to provide a powder composition produced by surface treatment using this copolymer or the like.

The novel copolymer of the present invention is useful as a cosmetic raw material. By also blending into the cosmetic of other cosmetic raw materials (such as various types of powders, oil agents, or the like), it is possible to provide surface protection characteristics, appearance, and feel of use that are further excellent from the standpoints of water resistance, sebum resistance, gloss, feel, adhesion to hair, adhesion to skin, or the like.

DESCRIPTION OF EMBODIMENTS

The novel copolymer of the present invention is a copolymer that includes: (A) a polymer having a carbosiloxane dendrimer structure represented by the following formula (1):

Formula 5

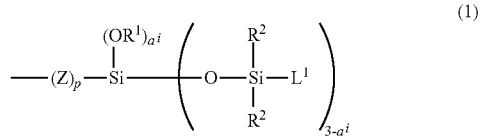

(1)

in the formula,
Z is a divalent organic group;
p is 0 or 1;
$R^1$ and $R^2$ each independently represent a group selected from the group consisting of alkyl groups, aryl groups, and aralkyl groups, having 1 to 10 carbon atoms; and
$L^1$ is a silylalkyl group, in the case of i=1, represented by the following formula (2):

Formula 6

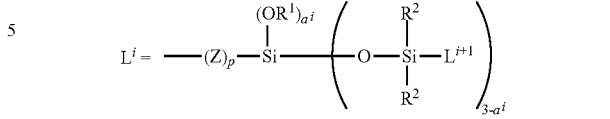

(2)

in the formula,
Z and p are the same as defined above;
$R^1$ and $R^2$ are the same as defined above;
i is an integer ranging from 1 to 10 indicating a total number of generations of the silylalkyl group, and i is preferably 1 to 5, more preferably 1 to 3, and further preferably 1 or 2;
$L^{i+1}$ is a group selected from the group consisting of a hydrogen atom, alkyl groups, aryl groups, and aralkyl groups, having 1 to 10 carbon atoms, and the silylalkyl groups; however, in the case of i=c (c is an integer ranging from 1 to 10 indicating the number of generations of the silylalkyl group, and c is preferably 1 to 5, more preferably 1 to 3, and further preferably 1 or 2), $L^{i+1}$ is a group selected from the group consisting of a hydrogen atom, alkyl groups, aryl groups, and aralkyl groups, having 1 to 10 carbon atoms; and in the case of i<c, $L^{i+1}$ is the silylalkyl group; and
$a^i$ is an integer ranging from 0 to 3, preferably 0 to 2, more preferably 0 to 1, and further preferably 0; and
(B) an unsaturated monomer having at least one hydrophilic group in the molecule;
the content of the unsaturated monomer having the carbosiloxane dendrimer structure being 35 to 50% by mass of the total monomer. Furthermore, the novel copolymer of the present invention preferably is a copolymer that includes (C) an unsaturated monomer having at least one fluorine-containing organic group in the molecule.

The mass fraction (i.e. {mass of the component (A)/mass of all monomers}) of the component (A) composing the novel copolymer of the present invention must be in the range of 0.35 to 0.50. This means that the copolymer has the (A) unsaturated monomer having the carbosiloxane dendrimer structure content in the range of 35 to 50% by mass of all monomer units. The mass fraction of the component (A) is preferably in the range of 40 to 50% by mass of all monomer units, and most preferably is in the range of 42 to 48% by mass of all monomer units.

When the mass fraction of the component (A) exceeds the upper limit, water repellency becomes excessively high, and compounding stability in the cosmetic or the like may become insufficient. When the mass fraction of the component (A) is less than the lower limit, water repellency and dispersion stability of the powder or the like on the skin may become insufficient. Moreover, the component (B) is a component for imparting hydrophilicity to the novel copolymer. When the novel copolymer of the present invention is used as a surface treatment agent, the novel copolymer preferably has an appropriate degree of water repellency for the entire molecule. It is thus particularly preferred that {component (A) mass content/total monomer mass content} is greater than or equal to {component (B) mass content/total monomer mass content}.

The components (A) to (C) of the novel copolymer of the present invention are preferably polymerized in ranges such that {component (A) mass content/total monomer mass content}:{component (B) mass content/total monomer mass content}:{component (C) mass content/total monomer mass content} are equal to [0.35 to 0.50:0.01 to 0.40:0.00 to 0.60], respectively. Further, the component (C) is preferably a necessary ingredient, and these composition ranges are preferably [0.35 to 0.50:0.10 to 0.40:0.10 to 0.50], respectively. These composition ranges are particularly preferably [0.40 to 0.50:0.15 to 0.40:0.15 to 0.40], respectively. When polymerization of the various components is outside the aforementioned ranges, problems may occur such as lowering of dispersion, compounding stability, or the like of the powder particularly when blended in the final product, and dispersion failure on the skin after volatilization of an oil agent.

The component (A) is a polymer having the carbosiloxane dendrimer structure represented in the above Formula (1), and this structure will be explained below in detail.

No particular limitation is placed on the divalent organic group, and examples of the divalent organic group include substituted or unsubstituted, and linear or branched divalent hydrocarbon groups having 1 to 30 carbon atoms. Examples of the substituted or unsubstituted, and linear or branched divalent hydrocarbon group having 1 to 30 carbon atoms include: linear or branched alkylene groups having 1 to 30 carbon atoms such as the methylene group, dimethylene group, trimethylene group, tetramethylene group, pentamethylene group, hexamethylene group, heptamethylene group, octamethylene group, or the like; alkenylene groups having 2 to 30 carbon atoms such as the vinylene group, allylene group, butenylene group, hexenylene group, octenylene group, or the like; arylene groups having 6 to 30 carbon atoms such as the phenylene group, diphenylene group, or the like; alkylenearylene groups having 7 to 30 carbon atoms such as the dimethylenephenylene group or the like; and substituted groups thereof in which hydrogen atoms bonded to carbon atoms of the groups are at least partially substituted by a halogen atom such as a fluorine atom or the like, or an organic group containing the carbinol group, epoxy group, glycidyl group, acyl group, carboxyl group, amino group, methacryl group, mercapto group, amide group, oxyalkylene group, or the like. The divalent hydrocarbon group is preferably an unsubstituted divalent saturated hydrocarbon group having 1 to 30 carbon atoms, more preferably is a linear or branched alkylene group having 1 to 6 carbon atoms, and particular preferably is a dimethylene group.

For example, the divalent organic group may be a group selected from the following groups:

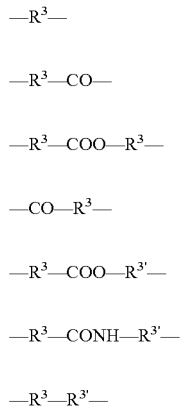

Formula 7 in the formula,
$R^3$ is the substituted or unsubstituted, and linear or branched divalent hydrocarbon group having 1 to 30 carbon atoms, which may have a substituent as described above; and
$R^{3'}$ is a group selected from the following groups:

Formula 8

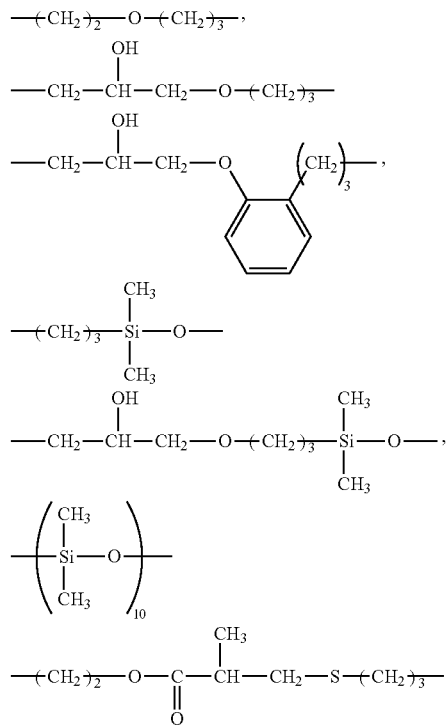

A divalent organic group represented by the general formula —$R^3$— or —$R^3$—$R^{3'}$—, which can be introduced by a reaction between a silicon-bonded hydrogen atoms and an alkenyl group, is preferred. In the same manner as described above, a divalent organic group represented by the general formula —$R^3$—COO—$R^3$— or —$R^3$—COO—$R^{3'}$—, which can be introduced by a reaction between a silicon-bonded hydrogen atom and an unsaturated carboxylic acid functional group, is also preferred.

In particular, Z is preferably a linear or branched alkylene group having 1 to 30 carbon atoms, and particularly preferably is the dimethylene group (ethylene group).

Examples of alkyl groups, aryl groups, or aralkyl groups having 1 to 10 carbon atoms include: linear or branched alkyl groups having 1 to 30 carbon atoms such as the methyl group, ethyl group, propyl group, butyl group, pentyl group, hexyl group, heptyl group, octyl group, and the like; cycloalkyl groups having 3 to 10 carbon atoms such as the cyclopentyl group, cyclohexyl group, and the like; aryl groups having 6 to 10 carbon atoms such as the phenyl group, tolyl group, xylyl group, and the like; aralkyl groups having 7 to 10 carbon atoms such as the benzyl group and the like; and substituted groups thereof in which hydrogen atoms bonded to carbon atoms of the groups are at least partially substituted by a halogen atom such as a fluorine atom and the like, or an organic group containing the carbinol group, epoxy group, glycidyl group, acyl group, carboxyl group, amino group, methacryl group, mercapto group, amide group, oxyalkylene group, and the like. The alkyl groups, aryl groups or aralkyl groups are preferably unsubstituted alkyl groups, aryl groups or aralkyl groups having from 1 to 10 carbon atoms, more preferably unsubstituted alkyl groups or aryl groups having from 1 to 6 carbon atoms, and even more preferably a methyl group, ethyl group, or phenyl group.

The carbosiloxane dendrimer structure is a chemical structure radially and highly branched from one silicon atom. The "i" specifying the total number of generations of the silylalkyl group indicates the degree of branching. For example, in the case in which the total number of generations i is 1 and $L^{i+1}$ is, for example, a methyl group, the carbosiloxane dendrimer structure means the following structure:

Formula 9

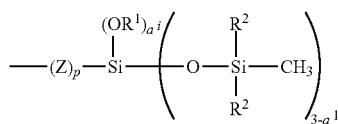
(2-1)

in the formula, Z, p, $R^1$, and $R^2$ are the same as defined above; and $a^1$ is an integer ranging from 0 to 3.

In the same manner as described above, in the case in which the number of generations i is 2 and $L^{i+1}$ is, for example, a methyl group, the carbosiloxane dendrimer structure means the following structure (where p=1):

Formula 10

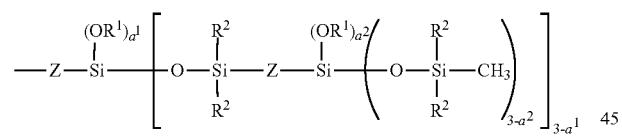
(2-2)

in the formula, Z, $R^1$, and $R^2$ are the same as defined above; and $a^1$ and $a^2$ are integers ranging from 0 to 3.

Further, in the case in which the number of generations i is 3 and $L^{i+1}$ is, for example, a methyl group, the carbosiloxane dendrimer structure means the following structure (where p=1):

Formula 11

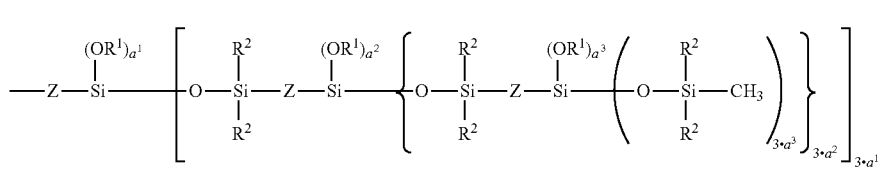
(2-3)

in the formula, Z, $R^1$, and $R^2$ are the same as defined above; and $a^1$, $a^2$, and $a^3$ are integers ranging from 0 to 3.

The following structures are particularly preferred as the carbosiloxane dendrimer structure:

Formula 12

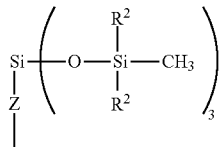

in the formula, Z and $R^2$ are the same as defined above,

Formula 13

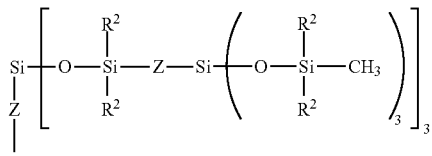

in the formula, Z and $R^2$ are the same as defined above.

The silylalkyl group having the carbosiloxane dendrimer structure has a structure in which the carbosiloxane units are extended in the form of a dendrimer. For this reason, the silylalkyl group is a functional group exhibiting increased water repellency (increased water resistance) in comparison to linear or simply branched polysiloxane units. Additionally, the silylalkyl group having a carbosiloxane dendrimer structure is chemically stable, and for this reason, the silylalkyl group is a functional group providing advantageous properties such as usability in combination with a wide range of raw materials for use in cosmetic compositions.

The (A) unsaturated monomer having the carbosiloxane dendrimer structure, for example, is represented by the following formula (1'):

Formula 14

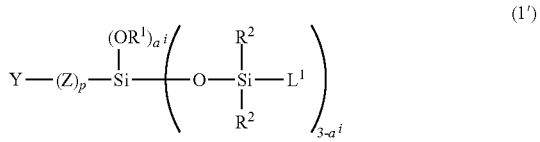
(1')

In the formula,
Y is an unsaturation-containing group capable of radical polymerization; and
Z, p, $R^1$, $R^2$, $L^1$, and $a^i$ are the same as defined above.

The unsaturation-containing group is not particularly restricted as long as the unsaturation-containing group has a radically polymerizable unsaturation. The unsaturation-containing group is exemplified by the vinyl group, allyl group, (meth)acryl group, or the like.

The (A) unsaturated monomer having the carbosiloxane dendrimer structure preferably has a group selected from the group including: an acryl or methacryl group-containing organic group represented by the following general formula:

Formula 15

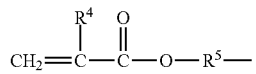

(in the formula, $R^4$ is a hydrogen atom or a methyl group; and $R^5$ is an alkylene group having 1 to 10 carbon atoms), an acryl or methacryl group-containing organic group represented by the following general formula:

Formula 16

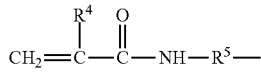

(in the formula, $R^4$ and $R^5$ have the same meaning as defined above), and an alkenylaryl group-containing organic group, or alkenyl group having 2 to 10 carbon atoms as represented by the following general formula:

Formula 17

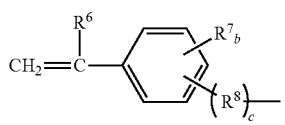

(in the formula, $R^6$ is a hydrogen atom or a methyl group; $R^7$ is an alkyl group having 1 to 10 carbon atoms; $R^8$ is an alkylene group having 1 to 10 carbon atoms; b is an integer ranging from 0 to 4, and c is either 0 or 1).

The (A) unsaturated monomer having the carbosiloxane dendrimer structure is exemplified by the following formulae.

Formula 18

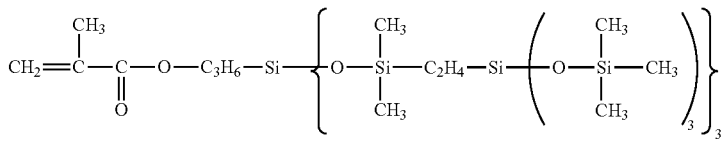

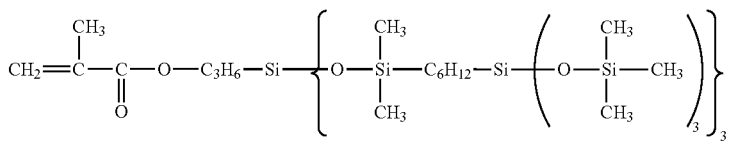

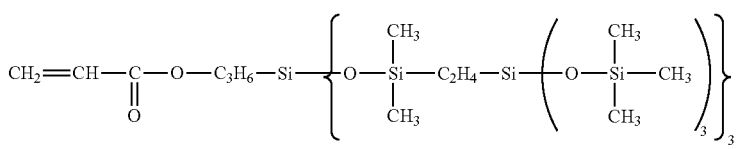

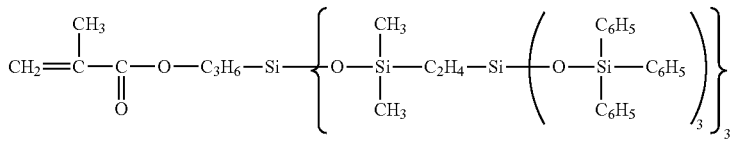

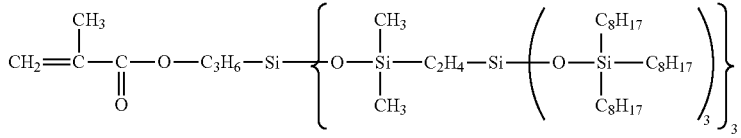

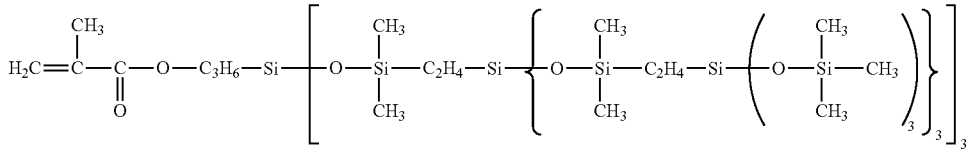

-continued

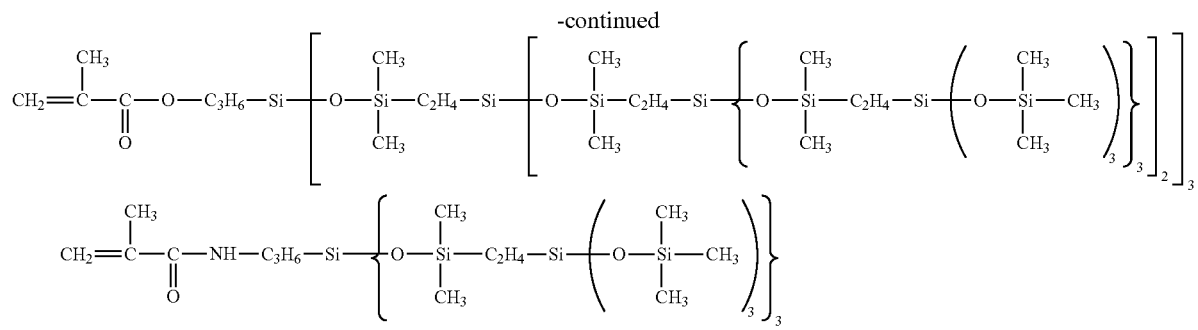

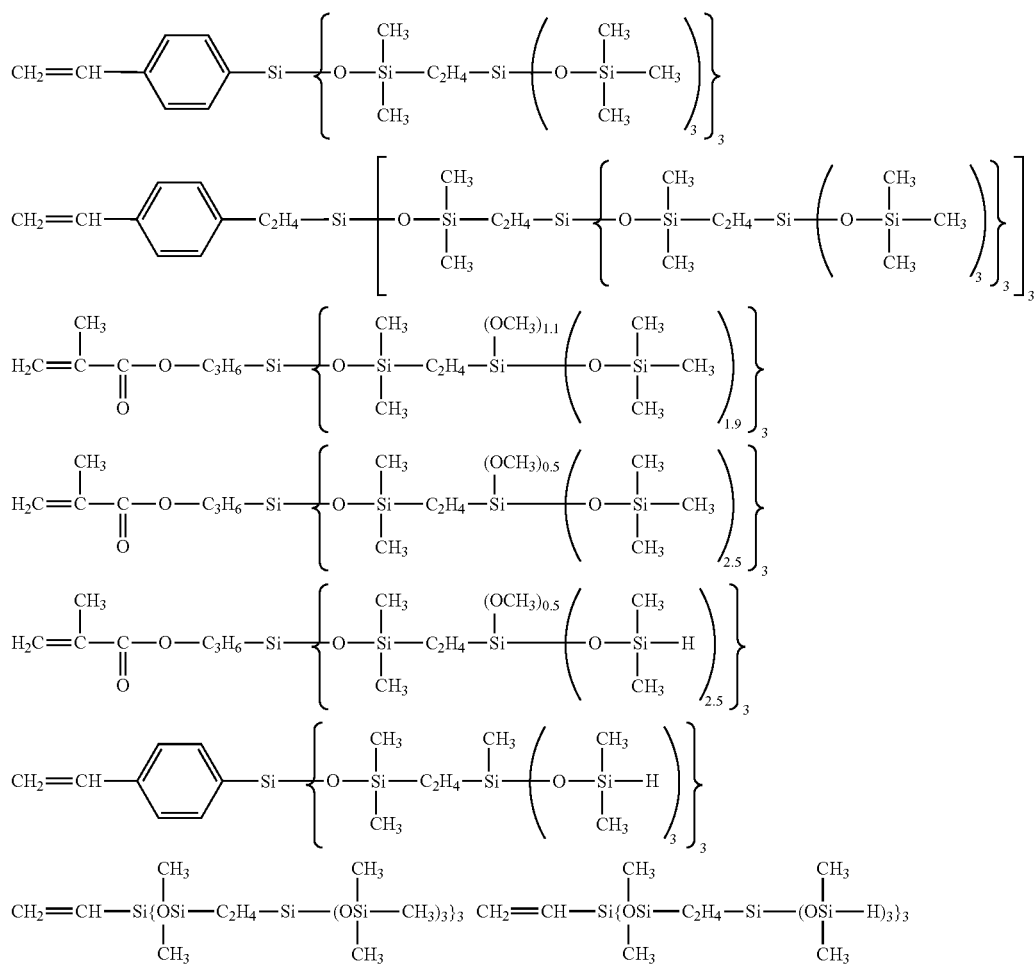

The (A) unsaturated monomer having the carbosiloxane dendrimer structure can be produced in accordance with, for example, a method for producing a branched siloxane/silalkylene copolymer described in Japanese Unexamined Patent Application Publication No. H11-001530 (Japanese Patent Application No. H09-171154).

No particular limitation is placed on the (B) unsaturated monomer having at least one hydrophilic group in the molecule, as long as the (B) unsaturated monomer having at least one hydrophilic group in the molecule has a linear or branched hydrophilic group and unsaturated radical-polymerizable group. Further, the component (B) may be one type of unsaturated monomer or a mixture of two or more types of different unsaturated monomers. Further, the hydrophilic group is preferably a hydrophilic group having an alcoholic hydroxyl group. The hydrophilic group is particularly preferably a monohydric or polyhydric alcoholic hydroxyl group.

The (B1) unsaturated monomer having at least one monohydric or polyhydric alcoholic hydroxyl group in the molecule is particularly preferably used as the component (B) of the present invention, and specific examples include: 2-hydroxyethyl acrylate, diethylene glycol acrylate, polyethylene glycol acrylate, methoxydiethylene glycol acrylate, methoxypolyethylene glycol acrylate, ethoxydiethylene glycol acrylate, ethoxypolyethylene glycol acrylate, 2-hydroxypropyl acrylate, dipropylene glycol acrylate, polypropylene glycol acrylate, methoxypolypropylene glycol acrylate, ethoxypolypropylene glycol acrylate, or similar monoacrylates; diethylene glycol diacrylate, polyethylene glycol diacrylate, or similar diacrylates; 2-hydroxyethyl methacrylate, diethylene glycol methacrylate, polyethylene glycol methacrylate, methoxydiethylene glycol methacrylate, methoxypolyethylene glycol methacrylate, ethoxydiethylene glycol methacrylate, ethoxypolyethylene glycol methacrylate, 2-hydroxypropyl methacrylate, dipropylene glycol methacrylate, polypropylene glycol methacrylate, methoxypolypropylene glycol methacrylate, ethoxypolypropylene glycol methacrylate, or similar mono-methacrylates; diethylene glycol dimethacrylate, polyethylene glycol dimethacrylate, dipropylene glycol dimethacrylate, polypropylene glycol dimethacrylate, or similar dimethacrylates; glyceryl acrylate, glyceryl methacrylate, or similar glyceryl acrylates; or the like. In particular, hydroxyalkyl esters of acrylic acid or methacrylic acid having 2 to 8 carbon atoms, or glyceryl esters of acrylic acid or methacrylic acid, are preferred as the component (B1).

The component (B1) is particularly preferably blended in a content range of 1 to 40% by mass of the total monomer units of the novel copolymer of the present invention, this range is more preferably 10 to 40% by mass, and this range is most preferably 15 to 40% by mass. The component (B) is a component that imparts suitable hydrophilicity to the copolymer of the present invention. When the polymerization range is outside the aforementioned range, problems may occur such as lowering of compounding stability, dispersibility of the powder, or the like when the copolymer is blended in the final product, and the occurrence of dispersion failure on the skin after volatilization of an oil agent.

The component (C) is an unsaturated monomer having at least one fluorine-containing organic group in the molecule. From the standpoints of improving water repellency and compatibility with water-repellency treated powder, a vinyl-based monomer containing a fluorinated organic group is particularly preferably used.

The vinyl-based monomer containing a fluorinated organic group is preferably one represented by the (C1) general formula: $CH_2=CR^{15}COOR^f$. In the formula, $R^{15}$ is a hydrogen atom or a methyl group, and $R^f$ is a fluorinated organic group. Examples include a fluoroalkyl group or a fluoroalkyloxyfluoroalkylene group, as described above. The compounds represented by the following formulae may be cited as examples of this type of component (C1). In the following formulae, z is an integer ranging from 1 to 4.

$CH_2=CCH_3COO—CF_3$, $CH_2=CCH_3COO—C_2F_5$, $CH_2=CCH_3COO-nC_3F_7$, $CH_2=CCH_3COO—CF(CF_3)_2$, $CH_2=CCH_3COO-nC_4F_9$, $CH_2=CCH_3COO—CF_2CF(CF_3)_2$, $CH_2=CCH_3COO-nC_5F_{11}$, $CH_2=CCH_3COO-nC_6F_{13}$, $CH_2=CCH_3COO-nC_8F_{17}$, $CH_2=CCH_3COO—CH_2CF_3$, $CH_2=CCH_3COO—CH(CF_3)_2$, $CH_2=CCH_3COO—CH_2CH(CF_3)_2$, $CH_2=CCH_3COO—CH_2(CF_2)_2F$, $CH_2=CCH_3COO—CH_2(CF_2)_3F$, $CH_2=CCH_3COO—CH_2(CF_2)_4F$, $CH_2=CCH_3COO—CH_2(CF_2)_6F$, $CH_2=CCH_3COO—CH_2(CF_2)_8F$, $CH_2=CCH_3COO—CH_2CH_2CF_3$, $CH_2=CCH_3COO—CH_2CH_2(CF_2)_2F$, $CH_2=CCH_3COO—CH_2CH_2(CF_2)_3F$, $CH_2=CCH_3COO—CH_2CH_2(CF_2)_4F$, $CH_2=CCH_3COO—CH_2CH_2(CF_2)_6F$, $CH_2=CCH_3COO—CH_2CH_2(CF_2)_8F$, $CH_2=CCH_3COO—CH_2CH_2(CF_2)_{10}F$, $CH_2=CCH_3COO—CH_2CH_2(CF_2)_{12}F$, $CH_2=CCH_3COO—CH_2CH_2(CF_2)_{14}F$, $CH_2=CCH_3COO—CH_2CH_2(CF_2)_{16}F$, $CH_2=CCH_3COO—CH_2CH_2CH_2CF_3$, $CH_2=CCH_3COO—CH_2CH_2CH_2(CF_2)_2F$, $CH_2=CCH_3COO—CH_2CH_2CH_2(CF_2)_2H$, $CH_2=CCH_3COO—CH_2(CF_2)_4H$, $CH_2=CCH_3COO—CH_2CH_2(CF_2)_3H$, $CH_2=CCH_3COO—CH_2CH_2CF(CF_3)—[OCF_2CF(CF_3)]_z—OC_3F_7$, $CH_2=CCH_3COO—CH_2CH_2CF_2CF_2—[OCF_2CF(CF_3)]_z—OC_3F_7$, $CH_2=CHCOO—CF_3$, $CH_2=CHCOO—C_2F_5$, $CH_2=CHCOO-nC_3F_7$, $CH_2=CHCOO—CF(CF_3)_2$, $CH_2=CHCOO-nC_4F_9$, $CH_2=CHCOO—CF_2CF(CF_3)_2$, $CH_2=CHCOO-nC_5F_{11}$, $CH_2=CHCOO-nC_6F_{13}$, $CH_2=CHCOO-nC_8F_{17}$, $CH_2=CHCOO—CH_2CF_3$, $CH_2=CHCOO—CH(CF_3)_2$, $CH_2=CHCOO—CH_2CH(CF_3)_2$, $CH_2=CHCOO—CH_2(CF_2)_2F$, $CH_2=CHCOO—CH_2(CF_2)_3F$, $CH_2=CHCOO—CH_2(CF_2)_4F$, $CH_2=CHCOO—CH_2(CF_2)_6F$, $CH_2=CHCOO—CH_2(CF_2)_8F$, $CH_2=CHCOO—CH_2CH_2CF_3$, $CH_2=CHCOO—CH_2CH_2(CF_2)_2F$, $CH_2=CHCOO—CH_2CH_2(CF_2)_3F$, $CH_2=CHCOO—CH_2CH_2(CF_2)_4F$, $CH_2=CHCOO—CH_2CH_2(CF_2)_6F$, $CH_2=CHCOO—CH_2CH_2(CF_2)_8F$, $CH_2=CHCOO—CH_2CH_2(CF_2)_{10}F$, $CH_2=CHCOO—CH_2CH_2(CF_2)_{12}F$, $CH_2=CHCOO—CH_2CH_2(CF_2)_{14}F$, $CH_2=CHCOO—CH_2CH_2(CF_2)_{16}F$, $CH_2=CHCOO—CH_2CH_2CH_2CF_3$, $CH_2=CHCOO—CH_2CH_2CH_2(CF_2)_2F$, $CH_2=CHCOO—CH_2CH_2CH_2(CF_2)_2H$, $CH_2=CHCOO—CH_2(CF_2)_4H$, $CH_2=CHCOO—CH_2CH_2(CF_2)_3H$, $CH_2=CHCOO—CH_2CH_2CF(CF_3)—[OCF_2CF(CF_3)]_z—OC_3F_7$, and $CH_2=CHCOO—CH_2CH_2CF_2CF_2—[OCF_2CF(CF_3)]_z—OC_3F_7$. Among these, the vinyl monomers represented by the following formulae are preferred. $CH_2=CHCOO—CH_2CH_2(CF_2)_6F$, $CH_2=CHCOO—CH_2CH_2(CF_2)_8F$, $CH_2=CCH_3COO—CH_2CH_2(CF_2)_6F$, $CH_2=CCH_3COO—CH_2CH_2(CF_2)_8F$, $CH_2=CHCOO—CH_2CF_3$, and $CH_2=CCH_3COO—CH_2CF_3$. The vinyl monomers represented by the following formulae are particularly preferred. $CH_2=CHCOO—CH_2CF_3$, and $CH_2=CCH_3COO—CH_2CF_3$.

The blended amount of the component (C1) in the total monomer units of the novel copolymer of the present invention is preferably in the range of 1 to 50% by mass, further preferably is in the range of 10 to 50% by mass, and most preferably is in the range of 15 to 40% by mass.

A radical polymerization method or an ion polymerization method may be used as the copolymerization method. Among these methods, the radical polymerization method is preferred, and a solution polymerization method is particularly preferably used. The solution polymerization method is carried out by reacting each of the unsaturated monomers in a solvent in the presence of a radical initiator for 3 to 20 hours under temperature conditions ranging from 50 to 150° C. The utilized solvents during such reaction are exemplified by aliphatic hydrocarbons such as hexane, octane, decane, cyclohexane, or the like; aromatic hydrocarbons such as benzene, toluene, xylene, or the like; ethers such as diethyl ether, dibutyl ether, tetrahydrofuran, dioxane, or the like; ketones such as acetone, methyl ethyl ketone, methyl isobutyl ketone, diisobutyl ketone, or the like; esters such as methyl acetate, ethyl acetate, butyl acetate, isobutyl acetate, or the like; alcohols such as methanol, ethanol, isopropyl alcohol, butanol, or the like; and organosiloxane oligomers such as octamethylcyclotetrasiloxane, decamethyl cyclopentasiloxane, hexamethyldisiloxane, octamethyltrisiloxane, or the like. Any conventionally known compound generally used in the radical polymerization method can be employed as the radical initiator. Specific examples of the radical initiator include azobis-based compounds such as 2,2'-azobis(isobutyronitrile), 2,2'-azobis(2-methylbutyronitrile), 2,2'-azobis(2,4-dimethylvaleronitrile), dimethyl-2,2'-azobis (2-methyl propionate), or the like; and organic peroxides such as benzoyl peroxide, lauroyl peroxide, tert-butyl peroxybenzoate, tert-butyl peroxy-2-ethylhexanoate, or the like. The radical initiators may be used alone or in combination of two or more types thereof. The utilized amount of the radical initiator preferably ranges from 0.1 to 5 parts by weight with respect to 100 parts by weight of the total of the components (A) to (C). Moreover, a chain transfer agent can be added during the polymerization. Specific examples of the chain transfer agent include mercapto compounds such as 2-mercaptoethanol, butyl mercaptan, n-dodecyl mercaptan, 3-mercaptopropyltrimethoxysilane, polydimethylsiloxanes having a mercaptopropyl group, or the like; and halogenated compounds such as methylene chloride, chloroform, carbon tetrachloride, butyl bromide, 3-chloropropyltrimethoxysilane, or the like.

After the polymerization, purification may be carried out by means of a method in which the remaining unreacted vinyl-based monomers are removed by heating under reduced pressure or a method in which a deodorant treatment due to a hydrogenation reaction without a solvent or with a solvent is carried out in the presence of a hydrogenation catalyst and light components are removed by distillation by contacting with nitrogen gas under reduced pressure. In particular, in the case of utilization as an external use preparation in which reduction of odors and miscibility with other cosmetic components are needed, the purified product is preferably used. In the hydrogenation reaction and stripping process, solvents, reaction conditions, pressure-reduction conditions, and the like used in the purification of conventional organopolysiloxane copolymers can be used or selected without any restrictions.

In order to greatly improve adhesive properties of the copolymer of the present invention with respect to skin or hair, or to provide appropriate cleansing properties after use, an amino group may be introduced into the side chain of the vinyl-based polymer by using an amino group-containing vinyl-based monomer such as dimethylaminoethyl acrylate, dimethylaminoethyl methacrylate, diethylaminoethyl acrylate, diethylaminoethyl methacrylate, or the like as part of the raw material monomers, followed by modification using an alkali metal salt, ammonium salt, or amine salt of a halogenated fatty acid such as the potassium salt of monochloroacetic acid, ammonium salt of monochloroacetic acid, aminomethylpropanol salt of monochloroacetic acid, triethanolamine salt of monobromoacetic acid, sodium salt of monochloropropionic acid, or the like. Alternatively, a carboxylic acid group may be introduced into the side chain of the vinyl-based polymer by using a carboxylic acid-containing vinyl-based monomer such as acrylic acid, methacrylic acid, itaconic acid, crotonic acid, fumaric acid, maleic acid or the like as part of the raw material monomers, followed by neutralization using an amine such as triethylamine, diethylamine, triethanolamine, or the like.

The weight average molecular weight of the copolymer preferably ranges from 3,000 to 2,000,000, and more preferably ranges from 5,000 to 800,000, from the standpoint of ease of blending in cosmetics. The form of the copolymer is exemplified by liquids, gums, pastes, solids, and powders. At the time of blending in cosmetics, the form of a solution or dispersion in which the copolymer is diluted with a solvent or a powder is preferred.

In particular, the copolymer of the present invention is preferably dispersed in (D) one or more types of oil agents, and the copolymer of the present invention is preferably used in the form of a liquid composition that includes at least one type of oil agent. Examples of the oil agents include animal oils, plant oils, synthetic oils, or the like that are generally used in cosmetics. As long as the oil agent is hydrophobic, the oil agent may be derived from any source, may be in the form of a solid, a semi-solid, or a liquid, and may be non-volatile, semi-volatile, or volatile. When the copolymer of the present invention is used in the form of the liquid composition, the component (D) is preferably entirely a liquid and has volatility. In particular, the oil agent is preferably one type, or a mixture of two or more types of oil agent selected from silicone oils, hydrocarbon oils, and fatty acid ester oils. When the oil agent is blended as two or more types of liquids and semi-solids (gum-like), an oil agent mixture in the form of a liquid as the overall is a useful form of the present invention from the standpoint of the ability to sufficiently form the liquid composition.

The copolymer of the present invention has particularly excellent miscibility with the oil agent, and a copolymer composition may be obtained that is uniform over a long time interval. This composition may be used itself as a surface treatment agent without modification. Alternatively, from the standpoints of handling ability and storage stability, this composition is extremely useful as a raw material for cosmetics. More particularly, a copolymer composition formed from 100 parts by mass of the copolymer of the present invention and 5 to 1,000 parts by mass of the oil agent, preferably 50 to 500 parts by mass of the oil agent, and more preferably 100 to 400 parts by mass of the oil agent, may be preferably used. In the case of obtaining the copolymer composition by diluting the copolymer of the present invention with the oil agent, a copolymer in which the solvent and unreacted monomers are removed after the polymerization reaction may be uniformly dispersed in the oil agent by means of mechanical force. Alternatively, the volatile solvent used in the polymerization reaction may be replaced by the oil agent.

Silicone oils are preferred as the oil agent. The silicone oils are hydrophobic as long as they are oil agents, and the molecular structure thereof may be a cyclic, linear, or branched structure. The viscosity of the silicone oils at 25° C. is usually in the range of 0.65 to 100,000 mm²/s, and preferably is in the range of 0.65 to 10,000 mm²/s. Particularly, when the copolymer of the present invention is used as a cosmetic raw material, by inclusion of at least one type of such silicone oils, it is possible to improve time-wise stability of the obtained cosmetic, and it is possible to realize the characteristic fresh feel of a silicone oil.

Specific examples of the silicone oils include cyclic organopolysiloxanes, linear organopolysiloxanes, and branched organopolysiloxanes. Among these example silicone oils, volatile linear organopolysiloxanes, branched organopolysiloxanes, and cyclic organopolysiloxanes are preferred. Volatile silicone oils composed of cyclic organopolysiloxanes are most appropriate.

The organopolysiloxanes represented by the following general formulae (3), (4), and (5) can be used as the silicone oils.

Formula 20

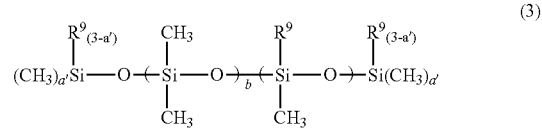

(3)

In the formulae,
R⁹ is a hydrogen atom, hydroxyl group, or a group selected from monovalent unsubstituted or fluorine- or amino-substituted alkyl groups, aryl groups, or alkoxy groups, having 1 to 30 carbon atoms, and groups represented by (CH₃)₃SiO{(CH₃)₂SiO}₁Si(CH₃)₂CH₂CH₂— (where I is an integer ranging from 0 to 1,000);
a' is an integer from 0 to 3;
b is an integer from 0 to 1,000; and
c' is an integer from 0 to 1,000, where $1 \leq b+c \leq 2{,}000$.

Formula 21

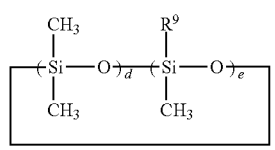

(4)

In this formula,
R⁹ is the same as described above;
d is an integer from 0 to 8; and
e is an integer from 0 to 8, where $3 \leq d+e \leq 8$.
Formula 22

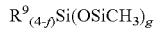

(5)

In this formula,
R⁹ is the same as described above;
f is an integer from 1 to 4; and
g is an integer from 0 to 500.

The monovalent, unsubstituted, or fluorine- or amino-substituted alkyl groups, aryl groups, and alkoxy groups, having 1 to 30 carbon atoms are exemplified by linear or branched alkyl groups having 1 to 30 carbon atoms such as the methyl group, ethyl group, propyl group, butyl group, pentyl group, hexyl group, heptyl group, octyl group, decyl group, dodecyl group, or the like; cycloalkyl groups having 3 to 30 carbon atoms such as the cyclopentyl group, cyclohexyl group, or the like; aryl groups having 6 to 30 carbon atoms such as the phenyl group, tolyl group, xylyl group, naphthyl group, or the like; alkoxy groups having 1 to 30 carbon atoms such as the methoxy group, ethoxy group, propoxy group, or the like; and substituted groups thereof, in which hydrogen atoms bonded to carbon atoms of the aforementioned groups are at least partially substituted by a fluorine atom or amino group. Unsubstituted alkyl groups or aryl groups are preferred, and an unsubstituted alkyl group having 1 to 6 carbon atoms or an aryl group is further preferred. A methyl group, ethyl group, or phenyl group is particularly preferred.

Specifically, examples of silicone oils having the structure described above include cyclic organopolysiloxanes such as hexamethyl cyclotrisiloxane (D3), octamethyl cyclotetrasiloxane (D4), decamethyl cyclopentasiloxane (D5), dodecamethyl-cyclohexasiloxane (D6), 1,1-diethylhexamethyl cyclotetrasiloxane, phenylheptamethyl cyclotetrasiloxane, 1,1-diphenylhexamethyl cyclotetrasiloxane, 1,3,5,7-tetravinyltetramethyl cyclotetrasiloxane, 1,3,5,7-tetramethyl cyclotetrasiloxane, 1,3,5,7-tetracyclohexyltetramethyl cyclotetrasiloxane, tris(3,3,3-trifluoropropyl) trimethylcyclotrisiloxane, 1,3,5,7-tetra(3-methacryloxypropyl) tetramethyl cyclotetrasiloxane, 1,3,5,7-tetra(3-acryloxypropyl) tetramethyl cyclotetrasiloxane, 1,3,5,7-tetra(3-carboxypropyl) tetramethyl cyclotetrasiloxane, 1,3,5,7-tetra(3-vinyloxypropyl) tetramethyl cyclotetrasiloxane, 1,3,5,7-tetra(p-vinylphenyl) tetramethyl cyclotetrasiloxane, 1,3,5,7-tetra[3-(p-vinylphenyl) propyl] tetramethyl cyclotetrasiloxane, 1,3,5,7-tetra(N-acryloyl-N-methyl-3-aminopropyl) tetramethyl cyclotetrasiloxane, 1,3,5,7-tetra(N,N-bis(lauroyl)-3-aminopropyl) tetramethyl cyclotetrasiloxane, and the like.

Examples of straight organopolysiloxanes include dimethylpolysiloxane in which both molecular terminals are capped with trimethylsiloxy groups (dimethylsilicone with a low viscosity such as 2 cst or 6 cst to dimethylsilicone with a high viscosity such as 1,000,000 cst), organohydrogenpolysiloxane, methylphenylpolysiloxane in which both molecular terminals are capped with trimethylsiloxy groups, a copolymer of methylphenylsiloxane and dimethylsiloxane in which both molecular terminals are capped with trimethylsiloxy groups, diphenylpolysiloxane in which both molecular terminals are capped with trimethylsiloxy groups, a copolymer of diphenylsiloxane and dimethylsiloxane in which both molecular terminals are capped with trimethylsiloxy groups, trimethylpentaphenyltrisiloxane, phenyl (trimethylsiloxy) siloxane, methylalkylpolysiloxane in which both molecular terminals are capped with trimethylsiloxy groups, a copolymer of methylalkylsiloxane and dimethylpolysiloxane in which both molecular terminals are capped with trimethylsiloxy groups, a copolymer of methyl (3,3,3-trifluoropropyl) siloxane and dimethylsiloxane in which both molecular terminals are capped with trimethylsiloxy groups, α,ω-dihydroxypolydimethylsiloxane, α,ω-diethoxypolydimethylsiloxane, 1,1,1,3,5,5,5-heptamethyl-3-octyltrisiloxane, 1,1,1,3,5,5,5-heptamethyl-3-dodecyltrisiloxane, 1,1,1,3,5,5,5-heptamethyl-3-hexadecyltrisiloxane, tristrimethylsiloxymethylsilane, tristrimethylsiloxyalkylsilane, tetrakistrimethylsiloxysilane, tetramethyl-1,3-dihydroxydisiloxane, octamethyl-1,7-dihydroxytetrasiloxane, hexamethyl-1,5-diethoxytrisiloxane, hexamethyldisiloxane, octamethyltrisiloxane, a higher alkoxy-modified silicone, a higher fatty acid-modified silicone, and the like.

Examples of branched organopolysiloxanes include methyltristrimethylsiloxysilane, ethyltristrimethylsiloxysilane, propyltristrimethylsiloxysilane, tetrakistrimethylsiloxysilane, phenyltristrimethylsiloxysilane, or the like.

Preferably, oil agents other than silicone oils are liquid at 5 to 100° C. Preferably, oil agents other than silicone oil are hydrocarbon oils and/or fatty ester oils. Such oil agents may be used alone or may be used together with the silicone oil.

When the copolymer of the present invention is used as a cosmetic raw material, by combined use of the hydrocarbon oil and/or fatty acid ester oil with the silicone oil, in addition to the characteristic fresh feel of the silicone oil, it is possible to retain the moisture on the skin and impart a smooth feel or moisture-retaining feel (also referred to as "moist feel") as if the skin or hair was wetted by the cosmetic. However, even when the copolymer of the present invention is used as a surface treatment agent, the copolymer of the present invention is advantageous in that time-wise stability of the cosmetic is not lost. Furthermore, with a cosmetic composition comprising the hydrocarbon oil and/or fatty acid ester oil and the silicone oil, these moisturizing components can be applied more stably and uniformly on the skin or hair, the moisturizing effects of the moisturizing component on the skin are improved and, compared to a cosmetic composition comprising only the oil agent other than the silicone oil (the hydrocarbon oil and/or fatty ester oil), a smoother, richer feeling to touch is imparted.

Examples of the hydrocarbon oil include liquid paraffin, light liquid isoparaffin, heavy liquid isoparaffin, vaseline, n-paraffin, isoparaffin, isododecane, isohexadecane, polyisobutylene, hydrogenated polyisobutylene, polybutene, ozokerite, ceresin, microcrystalline wax, paraffin wax, polyethylene wax, polyethylene/polypropylene wax, squalane, squalene, pristane, polyisoprene, and the like.

Examples of the fatty acid ester oil include hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl dimethyloctanoate, cetyl lactate, myristyl lactate, diethyl phthalate, dibutyl phthalate, lanolin acetate, ethylene glycol monostearate, propylene glycol monostearate, propylene glycol dioleate, glyceryl monostearate, glyceryl monooleate, glyceryl tri-2-ethylhexanoate, trimethylolpropane tri-2-ethylhexanoate, ditrimethylolpropane triethylhexanoate, ditrimethylolpropane isostearate/sebacate, trimethylolpropane trioctanoate, trimethylolpropane triisostearate, diisopropyl adipate, diisobutyl adipate, 2-hexyldecyl adipate, di-2-heptylundecyl adipate, diisostearyl malate, hydrogenated castor oil monoisostearate, N-alkylglycol monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum ester, ethyl oleate, octyldodecyl oleate, neopentylglycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyloctyl sebacate, cetyl palmitate, octyldodecyl palmitate, octyl palmitate, 2-ethylhexyl palmitate, 2-hexyldecyl palmitate, 2-heptylundecyl palmitate, cholesteryl 12-hydroxystearate, dipentaerythritol fatty acid ester, 2-hexyldecyl myristate, ethyl laurate, 2-octyldodecyl N-lauroyl-L-glutamate, di(cholesteryl/behenyl/octyldodecyl) N-lauroyl-L-glutamate, di(cholesteryl/octyldodecyl)N-lauroyl-L-glutamate, di(phytosteryl/behenyl/octyldodecyl)N-lauroyl-L-glutamate, di(phytosteryl/octyldodecyl) N-lauroyl-L-glutamate, isopropyl N-lauroylsarcosinate, diisostearyl malate, neopentylglycol dioctanoate, isodecyl neopentanoate, isotridecyl neopentanoate, isostearyl neopentanoate, isononyl isononanoate, isotridecyl isononanoate, octyl isononanoate, tridecyl isononanoate, diethylpentanediol dineopentanoate, methylpentanediol dineopentanoate, octyldodecyl neodecanoate, 2-butyl-2-ethyl-1,3-propanediol dioctanoate, pentaerythrityl tetraoctanoate, pentaerythrityl hydrogenated rosin, pentaerythrityl triethylhexanoate, dipentaerythrityl (hydroxystearate/stearate/rosinate), polyglyceryl tetraisostearate, polyglyceryl-10 nonaisostearate, polyglyceryl-8 deca (erucate/isostearate/ricinoleate) (hexyldecanoic acid/sebacic acid) diglyceryl oligoester, glycol distearate (ethylene glycol distearate), diisopropyl dimer dilinoleate, diisostearyl dimer dilinoleate, di(isostearyl/phytosteryl) dimer dilinoleate, (phytosteryl/behenyl) dimer dilinoleate, (phytosteryl/isostearyl/cetyl/stearyl/behenyl) dimer dilinoleate, dimer dilinoleyl dimer dilinoleate, dimer dilinoleyl diisostearate, dimer dilinoleyl hydrogenated rosin condensate, dimer dilinoleic acid hardened castor oil, hydroxyalkyl dimer dilinoleyl ether, glyceryl triisooctanoate, glyceryl triisostearate, glyceryl trimyristate, glyceryl triisopalmitate, glyceryl trioctanoate, glyceryl trioleate, glyceryl diisostearate, glyceryl tri(caprylate/caprate), glyceryl tri (caprylate/caprate/myristate/stearate), hydrogenated rosin triglyceride (hydrogenated ester gum), rosin triglyceride (ester gum), glyceryl behenate eicosane dioate, glyceryl di-2-heptylundecanoate, diglyceryl myristate isostearate, cholesteryl acetate, cholesteryl nonanoate, cholesteryl stearate, cholesteryl isostearate, cholesteryl oleate, cholesteryl 12-hydroxystearate, cholesteryl ester of macadamia nut oil fatty acid, phytosteryl ester of macadamia nut oil fatty acid, phytosteryl isostearate, cholesteryl ester of soft lanolin fatty acid, cholesteryl ester of hard lanolin fatty acid, cholesteryl ester of long-chain branched fatty acid, cholesteryl ester of long-chain α-hydroxy fatty acid, octyldodecyl ricinoleate, octyldodecyl ester of lanolin fatty acid, octyldodecyl erucate, isostearic acid hardened castor oil, ethyl ester of avocado fatty acid, isopropyl ester of lanolin fatty acid, and the like.

In addition to the above, fats and oils, higher alcohols, higher fatty acids, fluorine-based oils, or the like may be used in combination of two or more types thereof. For example, the oil agents described below may also be used in combination of two or more types. Hereinafter, the oil agents other than silicone oils, hydrocarbon oils, and fatty acid ester oils that can be used in the present invention will be described in detail.

Examples of such fats and oils include natural animal or plant fats and oils and semi-synthetic fats and oils such as avocado oil, linseed oil, almond oil, ibota wax, perilla oil, olive oil, cacao butter, kapok wax, kaya oil, carnauba wax, liver oil, candelilla wax, beef tallow, neatsfoot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shea butter, Chinese tung oil, cinnamon oil, jojoba wax, olive squalane, shellac wax, turtle oil, soybean oil, tea seed oil, camellia oil, evening primrose oil, corn oil, lard, rapeseed oil, Japanese tung oil, rice bran wax, germ oil, horse fat, persic oil, palm oil, palm kernel oil, castor oil, hydrogenated castor oil, castor oil fatty acid methyl ester, sunflower oil, grape oil, bayberry wax, jojoba oil, hydrogenated jojoba ester, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, reduced lanolin, lanolin alcohol, hard lanolin, lanolin acetate, lanolin fatty acid isopropyl ester, POE lanolin alcohol ether, POE lanolin alcohol acetate, lanolin fatty acid polyethylene glycol, POE hydrogenated lanolin alcohol ether, egg yolk oil, and the like. Herein, "POE" means "polyoxyethylene".

Examples of higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, POE cholesterol ether, monostearyl glycerol ether (batyl alcohol), monooleyl glycerol ether (selachyl alcohol), and the like.

Examples of higher fatty acids include lauric acid, myristic acid, palmitic acid, stearic acid, behenic acid, undecylenic acid, oleic acid, linolic acid, linolenic acid, arachidonic acid, eicosapentaenoic acid (EPA), docosahexaenoic acid (DHA), isostearic acid, 12-hydroxystearic acid, and the like.

Examples of the fluorine-based oil include perfluoropolyether, perfluorodecalin, perfluorooctane, and the like.

The copolymer is provided with film-forming ability. The copolymer is able to form a film on the surface of the powder and to change the surface properties of the powder to those of a water repellant powder. Thus the copolymer of the present invention or the liquid composition containing the copolymer of the present invention is particularly useful as a surface treatment agent and may be used with advantage for making a powder water repellent. Moreover, the copolymer is safe due to the lack of generation of hydrogen.

Use of the copolymer of the present invention as a surface treatment agent will be explained below in detail.

The surface treatment agent of the present invention is used with advantage for surface treatment of the (E) one or more type of powder or coloring agent, and particularly for surface treatment of any powder (including powders-pigments used as coloring agents) used in a cosmetic. The surface treatment agent of the present invention can provide a treated powder that has excellent feel of use, water resistance, sebum resistance, or the like. Any morphology (spherical, needle-shaped, plate-like, or the like), particle diameter (aerosol-like, fine particular, pigment-sized, or the like), or particle structure (porous, non-porous, or the like) is permissible and can be used as the powder and coloring agent as long as the powder and coloring agent is normally used in cosmetics. The powder or coloring agent is exemplified by inorganic powders, organic powders, surfactant metal salt powders, colored pigments, pearl pigments, metal powder pigments, tar pigments, natural pigments, or the like. The powder or the like is preferably at least one type selected from the group of inorganic pigment powders, organic pigment powders, and resin powders that have an average particle diameter in the range of 1 nm to 20 μm.

Furthermore, the powder or the like is preferably partially or entirely subjected to a surface treatment such as a water-repellent treatment, a hydrophilization treatment, or the like. Note that these powders may be compounded. Specifically, a powder or the like that have been surface treated using a fluorine compound, a surfactant, a thickening agent, or the like can be used. One or two or more types thereof can be used as necessary. Specifically, the powder or the like is preferably subjected to a water-repellent treatment.

The water-repellent treatment is not particularly limited, and examples thereof include various treatments in which the powder or the like is surface treated with a water repellency agent. Specific examples thereof include silicone treatments such as a methylhydrogenpolysiloxane treatment, a silicone resin treatment, a silicone gum treatment, an acryl silicone treatment, a fluorinated silicone treatment, and the like; metallic soap treatments such as a zinc stearate treatment and the like; silane treatments such as a silane coupling agent treatment, an alkylsilane treatment, and the like; fluorine compound treatments such as a perfluoroalkylsilane treatment, a perfluoroalkyl phosphate treatment, a perfluoro polyether treatment, and the like; amino acid treatments such as an N-lauroyl-L-lysine treatment and the like; oil agent treatments such as a squalane treatment and the like; and acryl treatments such as an alkyl acrylate treatment and the like. A combination of two or more of the treatments described above can be used.

Most preferably, the powder or the like used in the present invention is treated using a fluorinated compound such as a perfluoroalkylsilane, a perfluoroalkyl phosphate, a perfluoro polyether, or the like, or is silicone treated by methylhydrogenpolysiloxane treatment, silicone resin treatment, silicone gum treatment, acryl silicone treatment, fluorinated silicone treatment, or the like to produce the (E1) water-repellency treated powder or coloring agent.

Specific examples of the powders or coloring agents include inorganic powders, organic powders, surfactant metal salt powders (metallic soaps), colored pigments, pearl pigments, metal powder pigments, silicone elastomer powders, or the like. In addition, composite products of these pigments may also be used. Further, this powder or coloring agent includes powders and coloring agents that function as an ultraviolet light blocking component.

More particularly, examples of inorganic powders include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, black mica, lithia mica, silicic acid, silicic acid anhydride, aluminum silicate, magnesium silicate, aluminum magnesium silicate, calcium silicate, barium silicate, strontium silicate, metal salts of tungstic acid, hydroxyapatite, vermiculite, higilite, bentonite, montmorillonite, hectorite, zeolite, ceramic powder, dicalcium phosphate, alumina, aluminum hydroxide, boron nitride, silica, or the like. Examples of organic powders include polyamide powder, polyester powder, polyethylene powder, polypropylene powder, polystyrene powder, polyurethane powder, benzoguanamine powder, polymethylbenzoguanamine powder, tetrafluoroethylene powder, poly(methyl methacrylate) powder, cellulose, silk powder, nylon powder, nylon 12, nylon 6, silicone powder, copolymers of styrene and acrylic acid, copolymers of divinylbenzene and styrene, vinyl resin, urea resin, phenol resin, fluorine resin, silicon resin, acrylic resin, melamine resin, epoxy resin, polycarbonate resin, microcrystalline fiber powder, starch powder, lauroyl lysine, or the like. Examples of the surfactant metal salt powders (metallic soaps) include zinc stearate, aluminum stearate, calcium stearate, magnesium stearate, zinc myristate, magnesium myristate, zinc cetyl phosphate, calcium cetyl phosphate, sodium zinc cetyl phosphate, or the like. Examples of colored pigments include inorganic red pigments such as iron oxide, iron hydroxide, iron titanate or the like; inorganic brown pigments such as gamma-iron oxide or the like; inorganic yellow pigments such as yellow iron oxide, yellow ocher, or the like; inorganic black iron pigments such as black iron oxide, carbon black, or the like; inorganic purple pigments such as manganese violet, cobalt violet, or the like; inorganic green pigments such as chromium hydroxide, chromium oxide, cobalt oxide, cobalt titanate, and the like; inorganic blue pigments such as Prussian blue, ultramarine blue, and the like; lake-treated tar pigments, lake-treated natural pigments, and synthetic resin powders or the like produced as a composite of such powders; pearl pigments such as titanium oxide-coated mica, bismuth oxychloride, titanium oxide-coated bismuth oxychloride, titanium oxide-coated talc, fish scale foil, titanium oxide-coated colored mica, or the like; and metal powder pigments such as aluminum powder, copper powder, stainless steel powder, or the like. Examples of the tar pigments include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207, or the like. Examples of the natural pigments include carminic acid, laccaic acid, carthamin, brazilin, crocin, or the like.

The silicone elastomer powder is a crosslinked product of a straight diorganopolysiloxane formed principally from diorganosiloxy units (D units), and can be preferably obtained by crosslinking an organohydrogenpolysiloxane having a silicon-bonded hydrogen atom on the side chain or the molecular terminal and a diorganopolysiloxane having an unsaturated hydrocarbon group such as an alkenyl group and the like on the side chain or the molecular terminal, in the presence of a hydrosilylation reaction catalyst. Compared to a silicone resin powder formed from T units and Q units, the silicone elastomer powder is soft, has elasticity, and has superior oil absorbency. Therefore, oils and fats on the skin can be absorbed and makeup smearing can be prevented.

The silicone elastomer powder can be in various forms such as spherical, flat, amorphous, and the like. The silicone elastomer powder may be in the form of an oil dispersion. With the cosmetic composition of the present invention, a silicone elastomer powder having a particle shape, having a primary particle size in a range of 0.1 to 50 µm observed using an electron microscope and/or the average primary particle size in a range of 0.1 to 50 µm measured by laser diffraction/scattering method, and having spherical primary particles can be preferably compounded. The silicone elastomer that constitutes the silicone elastomer powder is preferably one having a hardness, as measured using a type A durometer in the "Rubber, Vulcanized or Thermoplastic—Determination of Hardness" specified in JIS K 6253, of 80 or lower, and more preferably 65 or lower.

The silicone elastomer powder may optionally be surface treated using silicone resin, silica, or the like. Examples of the surface treatment include those described in Japanese Unexamined Patent Application Publication Nos. H02-243612, H08-12545, H08-12546, H08-12524, H09-241511, H10-36219, H11-193331, and 2000-281523. Note that the crosslinking silicone powder as recited in "Standards of Cosmetic Components by Category" corresponds to the silicone elastomer powder. Commercially available products as the silicone elastomer powder are exemplified by Trefil E-506S, Trefil E-508, 9701 Cosmetic Powder, and 9702 Powder, manufactured by Dow Corning Toray Co., Ltd., or the like.

If the surface treatment agent of the present invention is used for surface treatment of a powder or the like, surface treatment may be carried out, for example, by a dry method using dry mixing of the surface treatment agent of the present invention and the powder undergoing treatment, or by a wet method in which the surface treatment agent of the present invention is dispersed in a solvent, the solvent mixture with the powder undergoing treatment is further wet mixed, and thereafter the treated powder is dried. However, the surface treatment method is not limited to these methods. Further, surface treatment may be carried out by diluting the surface treatment agent of the present invention in an oil agent used in cosmetics to produce the surface treatment agent of the present invention in the liquid composition form, and then mixing the liquid composition with the powder to form a slurry-like dispersion.

The wet method is preferred for surface treatment of the powder or the like using the surface treatment agent of the present invention. Any temperature may be used for mixing in the wet method, although the mixing temperature is preferably 60 to 80° C. Moreover, although the mixing time will vary depending on the amount of treated powder, the type of powder, or the like, the mixing time is normally 1 to 3 hours.

Although the utilized amount of the surface treatment agent of the present invention will vary according to the type of powder used for the surface treatment of powder or the like, generally, this utilized amount is preferably 1 to 10% by weight of the untreated powder, and further preferably is 1 to 5% by weight. When the utilized amount of the surface treatment agent is less than 1% by weight, the improvement effect of feel or the like may be insufficient when blended in a cosmetic. If the utilized amount of the surface treatment agent exceeds 10% by weight, and if the treated powder is blended in a cosmetic, there is concern that feel of use would worsen in that the cosmetic coating would become thick or the like.

The novel copolymer of the present invention is used as a copolymer that has a hydrophilic group and that has non-linear (i.e. highly branched) dendrimer-like silicone multi-grafted to the main chain. It is thus possible to use the novel copolymer of the present invention for surface treatment of a wide range of cosmetic powders or the like, and a powder composition may be obtained that includes the novel copolymer of the present invention and (E) one or more types of powders or coloring agents. The powder composition of the present invention has excellent dispersion stability of the powder or the like, flowability when used to make a slurry, handling ability, and compounding stability in cosmetics or the like. Further, when applied to the skin, the novel copolymer of the present invention is characterized as being capable of nearly completely suppressing dispersion failure of the powder or the like after volatilization of an oil agent, even when the powder or the like is produced by water-repellent treatment such as a fluorine-treated powder or coloring agent.

Since the novel copolymer of the present invention, and the liquid composition, the surface treatment agent, and the powder composition including the copolymer have the aforementioned characteristics, the novel copolymer of the present invention, the liquid composition, the surface treatment agent, and the powder composition including the copolymer are useful as cosmetic raw materials. By blending in a cosmetic together with other cosmetic raw materials such as various types of powders, oil agents, or the like, it is possible to provide excellent surface retention, appearance, and feel of use from the standpoints of water resistance, sebum resistance, gloss, feel, attachment to hair, attachment to skin, or the like.

When the novel copolymer of the present invention, or the liquid composition, the surface treatment agent, or the powder composition including the copolymer is blended in various types of cosmetics as a cosmetic raw material, the other types of cosmetic raw materials and types of blended cosmetics, for example, are the same as the cosmetic raw materials or the like disclosed in Japanese Unexamined Patent Application Publication No. 2011-148784, without particular limitation.

Specifically, at least one type of surfactant selected from the group including anionic surfactants, cationic surfactants, nonionic surfactants, and amphoteric surfactants may be also blended in a cosmetic together with the cosmetic raw material of the present invention. Specific examples of the surfactants are the same as those disclosed in paragraphs 0079 to 0084 of Japanese Unexamined Patent Application Publication No. 2011-148784 or the like, without particular limitation.

Further, in addition to the (D) one or more types of oil agents and the (E) one or more types of powders or coloring agents, the cosmetic raw material of the present invention may also include ingredients such as water-soluble polymers, oil-soluble gelling agents, organo-modified clay minerals, silicone gums, silicone resins, silicone elastomers, organic-modified silicones, ultraviolet light blocking components, or the like. Specific examples of such ingredients are the same as those disclosed in paragraphs 0087 to 0101 of Japanese Unexamined Patent Application Publication No. 2011-148784 or the like, without particular limitation.

At least one type of ultraviolet light blocking component selected from the group including fine particulate titanium oxide, fine particulate zinc oxide, 2-ethylhexyl p-methoxycinnamate, 4-tert-butyl-4'-methoxydibenzoylmethane, and benzophenone-based ultraviolet light absorbers is preferably blended in a cosmetic together with the cosmetic raw material of the present invention. Fluorine-treated fine particulate titanium oxide and fluorine-treated fine particulate zinc oxide are preferably blended in a cosmetic together with the cosmetic raw material of the present invention. These ultraviolet light blocking components are generally used, are easy to acquire, and have high ultraviolet light blocking effects and, thus can be beneficially used. In particular, using both inorganic and organic ultraviolet light blocking components is preferable, and using a UV-A blocking component in combination with a UV-B blocking component is more preferable.

Other ingredients normally used in cosmetics may be blended in a cosmetic together with the cosmetic raw material of the present invention within ranges so as not to impair the effects of the present invention. Such other ingredients are exemplified by alcohols, organic resins, moisturizing agents, preservatives, antimicrobial agents, perfumes, salts, antioxidants, pH adjusting agents, chelating agents, refreshing agents, anti-inflammatory agents, components for beautifying the skin (such as skin-lightening agents, cell activating agents, agents for ameliorating skin roughness, circulation promoters, astringents, antiseborrheic agents, or the like), vitamins, amino acids, nucleic acids, hormones, clathrate compounds, or the like. Specific examples of such ingredients are the same as those disclosed in paragraphs 0103 to 0116 or the like of Japanese Unexamined Patent Application Publication No. 2011-148784, without particular limitation.

The cosmetic raw material of the present invention, depending on the purposes thereof, may be blended with one type or two or more types of natural plant extract component, marine alga extract component, herbal extract, or the like in the cosmetic. Specific examples of such natural components are the same as those disclosed in paragraph 0119 or the like of Japanese Unexamined Patent Application Publication No. 2011-148784, without particular limitation Depending on the purposes thereof, in the cosmetic, the cosmetic raw material of the present invention may be blended with a solvent such as light isoparaffins, ethers, LPG, N-methylpyrrolidone, alternative chlorofluorocarbons, or the like in addition to water such as purified water, mineral water, or the like.

In addition to the copolymer of the present invention, the cosmetic raw materials of the present invention may include at least one type of component selected from the group including other acryl silicone dendrimer copolymers (including those disclosed in Japanese Unexamined Patent Application Publication No. 2011-148784 or the like), polyamide-modified silicones, alkyl-modified silicone waxes, and alkyl-modified silicone resin waxes. Specific examples of such components are the same as those disclosed in paragraphs 0122 to 0125 or the like of Japanese Unexamined Patent Application Publication No. 2011-148784, without particular limitation.

The cosmetic raw material of the present invention may be blended as the ingredient of cosmetics in any form, such as liquids, milky lotions, creams, solids, pastes, gels, powders, multilayers, mousses, sprays, or the like.

Without particular limitation, specific examples of products in which the cosmetic raw material of the present invention may be blended include skin care products such as skin cleaning agent products, skin care products, makeup products, anti-perspirant products, ultraviolet light blocking products, or the like; hair cosmetics such as hair washing products, hair styling products, hair dye products, baldness remedy products, hair rinse products, hair conditioning products, hair treatment products, or the like; bathing cosmetic products; hair regrowth agents, hair growth promoters, analgesics, germicides, anti-inflammatory agents, refreshing agents, and skin aging prevention agents.

The skin use cosmetic products can be used on any site of the entire body including the scalp, face (including lips, eyebrows, and cheeks), fingers, and fingernails. Specific examples thereof include cleansing gels, cleansing creams, cleansing foams, face washing creams, eye makeup removers, face washing foams, liquid soaps (body soaps), hand soaps, gel-like soaps, shaving creams, nail polish removers, acne treatment cosmetic compositions, and similar skin cleansing agent products; skin creams, scalp treatments, skin milks, milk lotions, emulsions, facial packs, body powders, essences, shaving lotions, massage lotions, and similar skin care products; foundations, liquid foundations, oil-based foundations, makeup bases, powders, face powders, cheek coloring, lip creams, lipsticks, lip glosses, eye creams, mascaras, eyebrow pencils, eyelash cosmetic products, and similar makeup products; deodorants and similar anti-perspirants; and sunscreen agents, tanning use medicaments (sun tanning agent), and similar ultraviolet light blocking products.

Examples of scalp use cosmetic products include shampoos, rinse-in shampoos, and similar hair use cleansing agents; hair waxes, hair use curl holding agents, setting agents, hair creams, hairsprays, hair liquids, and similar hair dressing products; hair coloring substances, hair color sprays, hair color rinses, hair color sticks, and similar hair use coloration products; hair tonics, hair treatment essences, hair packs, and similar hair growing products; and oil rinses, cream rinses, treatment rinses, hair conditioners, hair treatments, and similar hair rinse or hair conditioning products. In addition, examples of bath use cosmetic products include bath foams.

The copolymer of the present invention may be blended in non-cosmetic products for other applications such as various types of external use preparations, paints, coating agents, anti-foaming agents, deodorizing agents, or the like.

EXAMPLES

Hereinafter, the present invention is described in detail with reference to practical examples and comparative examples, but it should be understood that the present invention is not limited to these practical examples. The viscosity (kinetic viscosity) values are measured at 25° C.

Moreover, the molecular weight values indicate weight average molecular weight determined on a polystyrene basis using gel permeation chromatography (GPC), or are expressed as the ratio (Mw/Mn) of the weight average molecular weight divided by the number average molecular weight.

Practical Example 1

100 g of isopropyl alcohol (IPA) was placed in a 500 mL four-neck flask equipped with a stirrer, thermometer, and reflux condenser. Nitrogen gas was used for bubbling and performing sufficient degasification, and then the flask was heated to 80° C. 25 g of methyl methacrylate, 10 g of 2-ethylhexylacrylate, 20 g of hydroxyethyl methacrylate, 45 g of a carbosiloxane dendrimer monomer represented by the following formula (A), Formula 23

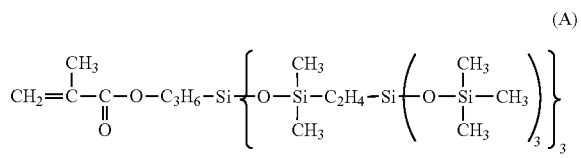

30 g of isopropyl alcohol, and 1.0 g of 2,2'-azobis-2-methylbutyronitrile (produced by Otsuka Chemical Co., Ltd.), were added to a dripping funnel, and the mixture was dissolved. While the monomer mixture was maintained at 80° C. under a nitrogen atmosphere, the dripping funnel was used for drop-wise addition over 2 hours. After completion of drop-wise addition, the mixture was stirred and heated for 6 hours under nitrogen atmosphere. After completion of stirring, the polymerization addition rate of the reaction products was analyzed by gas chromatography. As a result, the addition rate of polymerization was found to be 97%, and it was determined that a vinyl-based polymer was obtained. 250 g of decamethylpentacyclosiloxane was added to the isopropyl alcohol solution of the vinyl-based polymer. Then the IPA was removed by distillation at 120° C. The excess decamethylpentacyclosiloxane and unreacted monomers were removed by distillation under reduced pressure to adjust the solids content to 30% by weight. The weight average molecular weight of this polymer was 21,700, and Mw/Mn was 1.66.

Practical Example 2

The same procedure as that of Practical Example 1 was used except for addition to the dropping funnel of 18 g of methyl methacrylate, 7 g of 2-ethylhexylacrylate, 30 g of hydroxyethyl methacrylate, 45 g of the carbosiloxane dendrimer monomer represented by formula (A), and 1.0 g of 2,2'-azobis-2-methylbutyronitrile (produced by Otsuka Chemical Co., Ltd.). A decamethylpentasiloxane solution of vinyl polymer was obtained. The weight average molecular weight of this polymer was 12,800, and Mw/Mn was 2.24.

Practical Example 3

The same procedure as that of Practical Example 1 was used except for addition to the dropping funnel of 32 g of 2-ethylhexyl methacrylate, 5 g of 2-ethylhexylacrylate, 18 g of glyceryl methacrylate, 45 g of the carbosiloxane dendrimer monomer represented by formula (A), and 1.0 g of 2,2'-azobis-2-methylbutyronitrile (produced by Otsuka Chemical Co., Ltd.). A decamethylpentasiloxane solution of vinyl polymer was obtained.

Practical Example 4

The same procedure as that of Practical Example 1 was used except for addition to the dropping funnel of 20 g of trifluoroethyl methacrylate, 5 g of 2-ethylhexylacrylate, 30 g of hydroxyethyl methacrylate, 45 g of the carbosiloxane dendrimer monomer represented by formula (A), and 1.0 g of 2,2'-azobis-2-methylbutyronitrile (produced by Otsuka Chemical Co., Ltd.). A decamethylpentasiloxane solution of vinyl polymer was obtained. The weight average molecular weight of this polymer was 9,300, and Mw/Mn was 4.65.

Practical Example 5

The same procedure as that of Practical Example 1 was used except for addition to the dropping funnel of 16 g of trifluoroethyl methacrylate, 4 g of 2-ethylhexylacrylate, 35 g of hydroxyethyl methacrylate, 45 g of the carbosiloxane dendrimer monomer represented by formula (A), and 1.0 g of 2,2'-azobis-2-methylbutyronitrile (produced by Otsuka Chemical Co., Ltd.). A decamethylpentasiloxane solution of vinyl polymer was obtained.

Practical Example 6

The same procedure as that of Practical Example 1 was used except for addition to the dropping funnel of 42 g of methyl methacrylate, 10 g of 2-ethylhexylacrylate, 3 g of hydroxyethyl methacrylate, 45 g of the carbosiloxane dendrimer monomer represented by formula (A), and 1.0 g of 2,2'-azobis-2-methylbutyronitrile (produced by Otsuka Chemical Co., Ltd.). A decamethylpentasiloxane solution of vinyl polymer was obtained. The weight average molecular weight of this polymer was 73,300, and Mw/Mn was 3.35.

Practical Example 7

The same procedure as that of Practical Example 1 was used except for addition to the dropping funnel of 35 g of methyl methacrylate, 10 g of 2-ethylhexylacrylate, 10 g of hydroxyethyl methacrylate, 45 g of the carbosiloxane dendrimer monomer represented by formula (A), and 1.0 g of 2,2'-azobis-2-methylbutyronitrile (produced by Otsuka Chemical Co., Ltd.). A decamethylpentasiloxane solution of vinyl polymer was obtained. The weight average molecular weight of this polymer was 71,400, and Mw/Mn was 3.13.

Practical Example 8

The same procedure as that of Practical Example 1 was used except for addition to the dropping funnel of 32 g of trifluoroethyl methacrylate, 5 g of 2-ethylhexylacrylate, 18 g of glyceryl methacrylate, 45 g of the carbosiloxane dendrimer monomer represented by formula (A), and 1.0 g of 2,2'-azobis-2-methylbutyronitrile (produced by Otsuka Chemical Co., Ltd.). A decamethylpentasiloxane solution of vinyl polymer was obtained. The weight average molecular weight of this polymer was 6,080, and Mw/Mn was 3.38.

Comparative Example 1

The same procedure as that of Practical Example 1 was used except for addition to the dropping funnel of 36 g of methyl methacrylate, 14 g of 2-ethylhexylacrylate, 5 g of vinylacetamide, 45 g of the carbosiloxane dendrimer monomer represented by formula (A), and 1.0 g of 2,2'-azobis-2-methylbutyronitrile (produced by Otsuka Chemical Co., Ltd.). A decamethylpentasiloxane solution of vinyl polymer was obtained. The weight average molecular weight of this polymer was 79,000, and Mw/Mn was 3.35.

Comparative Example 2

The same procedure as that of Practical Example 1 was used except for addition to the dropping funnel of 25 g of methyl methacrylate, 25 g of 2-ethylhexylacrylate, 5 g of vinylacetamide, 45 g of the carbosiloxane dendrimer monomer represented by formula (A), and 1.0 g of 2,2'-azobis-2-methylbutyronitrile (produced by Otsuka Chemical Co., Ltd.). A decamethylpentasiloxane solution of vinyl polymer was obtained. The weight average molecular weight of this polymer was 91,100, and Mw/Mn was 4.07.

Evaluation Example 1

12 g of silicone-treated pigment grade titanium oxide (produced by Daito Kasei Kogyo Co., Ltd.), 1 g of the dispersing agent described in the practical examples, and 7 g of decamethylpentasiloxane were mixed using a disperser. An E-type rotary viscometer was used to measure viscosity, and dispersibility was evaluated. Results are shown in Table 1. The evaluation criteria are indicated as follows. Moreover, as Comparative Example 3, evaluation results obtained using FA 4001 CM Silicone Acrylate (produced by Dow Corning Toray Co., Ltd., abbreviated in the table as "FA 4001 CM") as the dispersing agent are shown.

Evaluation Criteria
•: Viscosity is less than or equal to 350 cP.
○: Viscosity is 350 to 600 cP.
Δ: Viscosity is greater than or equal to 600 cP.

Evaluation Example 2

12 g of silicone-treated fine particulate titanium oxide (produced by Tayca Corp.), 3 g of the dispersing agent described in the practical examples, and 15 g of decamethylpentasiloxane were mixed using a disperser. Zirconia beads (0.8 mm) were added, and the mixture was dispersed using a paint shaker. After dispersion, the zirconia beads were removed by filtration, an E-type rotary viscometer was used to measure viscosity, and dispersibility was evaluated. The evaluation criteria are indicated as follows. Moreover, as Comparative Example 3, evaluation results obtained using FA 4001 CM Silicone Acrylate (produced by Dow Corning Toray Co., Ltd., abbreviated in the table as "FA 4001 CM") as the dispersing agent are shown.

Evaluation Criteria
•: Viscosity is less than or equal to 1,500 cP.
○: Viscosity is 1,501 to 5,000 cP.
x: Gelation occurred.

TABLE 1

| | Practical examples (evaluations) | | | | | | | | Comparative examples (evaluations) | | |
|---|---|---|---|---|---|---|---|---|---|---|---|
| | 1 | 2 | 3 | 4 | 5 | 6 | 7 | 8 | 1 | 2 | 3 |
| Copolymer No. | 1 | 2 | 3 | 4 | 5 | 6 | 7 | 8 | 8 | 9 | "FA4001 CM" |
| Pigment viscosity | • | • | ○ | ○ | ○ | • | • | • | Δ | Δ | • |
| Fine particle viscosity | ○ | ○ | ○ | ○ | ○ | • | • | • | x | x | x |

INDUSTRIAL APPLICABILITY

The copolymer of the present invention according to the present application has excellent stability without generation of hydrogen. Highly branched (non-linear chain) dendrimer-shaped silicone is multi-grafted to the main chain of the copolymer, and the utilized copolymer has a hydrophilic group. Thus compatibility is good with various types of other organic compounds and powder raw materials, and use is possible in industrial applications outside the field of cosmetics. Without particular limitation, such applications are exemplified by varnishes and paint additives having excellent heat resistance, weathering resistance, and electrical characteristics; modification agents of various types of urethanes and foamed materials; demolding agents and separating agents; antifoam agents; grease and oil compounds; oils used as insulation, polishing agents, waterproofing agents, heating mediums, cooling mediums, lubricants, or the like; modification agents, surface treatment agents, and additives used for rubbers and resins; blending materials, modification agents, and precursors used for silane coupling agents; coating materials and sealing materials used for construction and lining applications; protective agents, lubricants, and buffer agents used for optical fibers and electrical lines; or the like.

The invention claimed is:

1. A copolymer comprising:
(A) an unsaturated monomer having a carbosiloxane dendrimer structure represented by the following formula (1):

[Formula 1]

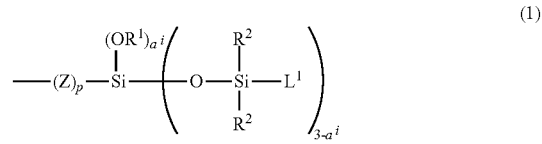

wherein,
Z is a divalent organic group;
p is 0 or 1;
$R^1$ and $R^2$ each independently represent a group selected from the group consisting of alkyl groups, aryl groups, and aralkyl groups, having 1 to 10 carbon atoms; and
$L^1$ is a silylalkyl group, in the case of i=1, represented by the following formula (2):

[Formula 2]

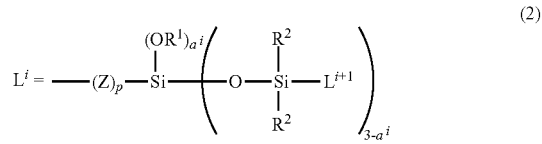

wherein,
Z and p are the same as defined above;
$R^1$ and $R^2$ are the same as defined above;
i is an integer ranging from 1 to 10 indicating a total number of generations of the silylalkyl group;
$L^{i+1}$ is a group selected from the group consisting of a hydrogen atom, alkyl groups, aryl groups, and aralkyl groups, having 1 to 10 carbon atoms, and the silylalkyl groups; however, in the case of i=c (where c is an integer ranging from 1 to 10 indicating the number of generations of the silylalkyl group), $L^{i+1}$ is a group selected from the group consisting of a hydrogen atom, alkyl groups, aryl groups, and aralkyl groups, having 1 to 10 carbon atoms; and in the case of i<c, $L^{i+1}$ is the silylalkyl group; and $a^i$ is an integer ranging from 0 to 3; and
(B) an unsaturated monomer having at least one hydrophilic group in the molecule;
the content of the unsaturated monomer having the carbosiloxane dendrimer structure being 35 to 50% by mass of the total monomer weight content in the copolymer.

2. The copolymer according to claim 1 wherein the (B) unsaturated monomer having at least one hydrophilic group in the molecule is (B1) an unsaturated monomer having a monohydric or polyhydric alcoholic hydroxyl group.

3. The copolymer according to claim 1 wherein the copolymer further comprises (C) an unsaturated monomer having at least one fluorine-containing organic group in the molecule.

4. The copolymer according to claim 1 wherein the copolymer is obtained by copolymerizing
the (A) unsaturated monomer having the carbosiloxane dendrimer structure,
the (B) unsaturated monomer having at least one hydrophilic group in the molecule, and optionally
an (C) unsaturated monomer having at least one fluorine-containing organic group in the molecule,
at weight ratio ranges such that component (A) weight content/total monomer weight content:component (B) weight content/total monomer weight content:component (C) weight content/total monomer weight content are in the ranges of 0.35 to 0.50:0.01 to 0.40:0.00 to 0.60, respectively; and
the following condition is fulfilled: component (A) weight content/total monomer weight content>component (B) weight content/total monomer weight content.

5. The copolymer according to claim 1 wherein the copolymer is obtained by copolymerizing
the (A) unsaturated monomer having the carbosiloxane dendrimer structure,
the (B) unsaturated monomer, which is (B1) an unsaturated monomer having at least one monohydric or polyhydric alcoholic hydroxyl group in the molecule, and
(C1) an unsaturated monomer represented by the general formula:

$CH_2=CR^5COOR^f$ wherein,
$R^5$ is a hydrogen atom or methyl group;
$R^f$ is a fluoroalkyl group or fluoroalkyloxyfluoroalkylene group,
at mass ratio ranges such that component (A) mass content/total monomer mass content:component (B1) mass content/total monomer mass content:component (C1) mass content/total monomer mass content are in the ranges of 0.35 to 0.50:0.10 to 0.40:0.10 to 0.50, respectively; and
the following condition is fulfilled: component (A) mass content/total monomer mass content≥component (B) mass content/total monomer mass content.

6. A liquid composition comprising:
the copolymer of claim 1; and
(D) at least one type of oil agent.

7. A surface treatment composition comprising the copolymer of claim 1.

8. A powder composition comprising:
the copolymer of claim 1; and
(E) at least one type of powder or coloring agent.

9. The powder composition according to claim 8 wherein the powder is (E1) a water-repellency treated powder or coloring agent.

10. A cosmetic raw material comprising the copolymer of claim 1.

11. A cosmetic raw material comprising the liquid composition of claim 6.

12. A cosmetic raw material comprising the powder composition of claim 8.

13. The copolymer according to claim 3 wherein the (C) unsaturated monomer having at least one fluorine-containing organic group in the molecule is (C1) an unsaturated monomer represented by the general formula:

$CH_2=CR^5COOR^f$ wherein,
$R^5$ is a hydrogen atom or methyl group;
$R^f$ is a fluoroalkyl group or fluoroalkyloxyfluoroalkylene group.

14. The copolymer according to claim 2 wherein the copolymer further comprises (C) an unsaturated monomer having at least one fluorine-containing organic group in the molecule.

15. The liquid composition according to claim 6 wherein the (D) at least one type of oil agent is hydrophobic silicone oil, a volatile silicone oil, a hydrocarbon oil, or combinations thereof.

16. The liquid composition according to claim 15 wherein the (D) at least one type of oil agent is the hydrophobic silicone oil, which has a viscosity of from 0.65 to 100,000 $mm^2$/s at 25° C.

* * * * *